US012286651B2

(12) United States Patent
Kurbanov

(10) Patent No.: US 12,286,651 B2
(45) Date of Patent: Apr. 29, 2025

(54) MUTANT DNA POLYMERASE(S) WITH IMPROVED STRAND DISPLACEMENT ABILITY

(71) Applicant: Roche Molecular Systems, Inc., Pleasanton, CA (US)

(72) Inventor: Feruz Kurbanov, Mountain View, CA (US)

( * ) Notice: Subject to any disclaimer, the term of this patent is extended or adjusted under 35 U.S.C. 154(b) by 0 days.

(21) Appl. No.: 18/219,045

(22) Filed: Jul. 6, 2023

(65) Prior Publication Data

US 2024/0110162 A1  Apr. 4, 2024

Related U.S. Application Data

(63) Continuation of application No. 17/274,667, filed as application No. PCT/EP2019/074320 on Sep. 12, 2019, now Pat. No. 11,739,306.

(60) Provisional application No. 62/730,908, filed on Sep. 13, 2018.

(51) Int. Cl.
*C12N 9/12* (2006.01)
*C12Q 1/6844* (2018.01)

(52) U.S. Cl.
CPC ......... *C12N 9/1252* (2013.01); *C12Q 1/6844* (2013.01); *C12Y 207/07007* (2013.01)

(58) Field of Classification Search
None
See application file for complete search history.

(56) References Cited

U.S. PATENT DOCUMENTS

| 8,026,091 B2 | 9/2011 | Bauer et al. |
| 10,563,182 B2 | 2/2020 | Bauer et al. |
| 2012/0208240 A1 | 8/2012 | Bauer |
| 2018/0135034 A1 | 5/2018 | Bauer |

FOREIGN PATENT DOCUMENTS

| WO | 2007076461 A1 | 7/2007 |
| WO | 2012110060 A1 | 8/2012 |

OTHER PUBLICATIONS

Uemori et al., J. Biochem., vol. 113, pp. 401-410, 1993.*
Gibbs et al., Molecular diversity and catalytic activity of Thermus DNA polymerases, Extremophiles 13:817-826, (2009).*
Ngo et al. in The Protein Folding Problem and Tertiary Structure Prediction, 1994, Merz et al. (ed.), Birkhauser, Boston, MA, pp. 433 and 492-495.*
Japanese Office Action issued Jul. 25, 2023 in Application No. 2021-514033, 5 pages.
Sousa, R., et al., A mutant T7 Rna polymerase as a DNA polymerase, The EMBO Journal, vol. 14, No. 18, pp. 4609-4621, 1995.
Zhu, H., et al., Interference Analysis of Dna Polymerases in Examining Gene Mutation With Pcr Technique, Environmental Chemistry, vol. 27.1, pp. 49-51, 2008.

* cited by examiner

*Primary Examiner* — Richard G Hutson
(74) *Attorney, Agent, or Firm* — Daniel E. Agnew

(57) ABSTRACT

Disclosed are DNA polymerases having increased 5'-3' strand displacement activity and substantially reduced 5'-3' exonuclease and endonuclease activity relative to a corresponding, unmodified polymerase. The polymerases are useful in a variety of disclosed primer extension methods. Also disclosed are related compositions, including recombinant nucleic acids, vectors, and host cells, which are useful, e.g., for production of the DNA polymerases.

16 Claims, 7 Drawing Sheets

Specification includes a Sequence Listing.

Fig. 1

| A. | Sequence identities over the entire polymerase I enzyme (corresponding to amino acids 1-834 of Z05) | | | | | | | | | | | | |
|---|---|---|---|---|---|---|---|---|---|---|---|---|---|
| Name | Z05 | Taq | Tfi | Tfl | Sps17 | Tth | Tca | Dra | Tma | Tne | Taf | Bst | Bca |
| Z05 |  | 0.864 | 0.833 | 0.859 | 0.839 | 0.962 | 0.958 | 0.459 | 0.374 | 0.368 | 0.359 | 0.407 | 0.408 |
| Taq | 0.864 |  | 0.831 | 0.854 | 0.836 | 0.872 | 0.864 | 0.468 | 0.382 | 0.368 | 0.351 | 0.397 | 0.397 |
| Tfi | 0.833 | 0.831 |  | 0.82 | 0.991 | 0.829 | 0.824 | 0.45 | 0.371 | 0.375 | 0.353 | 0.405 | 0.397 |
| Tfl | 0.859 | 0.854 | 0.82 |  | 0.824 | 0.853 | 0.848 | 0.462 | 0.381 | 0.374 | 0.356 | 0.397 | 0.398 |
| Sps17 | 0.839 | 0.836 | 0.991 | 0.824 |  | 0.835 | 0.83 | 0.452 | 0.375 | 0.377 | 0.355 | 0.407 | 0.399 |
| Tth | 0.962 | 0.872 | 0.829 | 0.853 | 0.835 |  | 0.989 | 0.463 | 0.373 | 0.367 | 0.358 | 0.406 | 0.406 |
| Tca | 0.958 | 0.864 | 0.824 | 0.848 | 0.83 | 0.989 |  | 0.46 | 0.371 | 0.365 | 0.356 | 0.404 | 0.404 |
| Dra | 0.459 | 0.468 | 0.45 | 0.462 | 0.452 | 0.463 | 0.46 |  | 0.334 | 0.325 | 0.314 | 0.338 | 0.339 |
| Tma | 0.374 | 0.382 | 0.371 | 0.381 | 0.375 | 0.373 | 0.371 | 0.334 |  | 0.854 | 0.567 | 0.37 | 0.377 |
| Tne | 0.368 | 0.368 | 0.375 | 0.374 | 0.377 | 0.367 | 0.365 | 0.325 | 0.854 |  | 0.558 | 0.377 | 0.376 |
| Taf | 0.359 | 0.351 | 0.353 | 0.356 | 0.355 | 0.358 | 0.356 | 0.314 | 0.567 | 0.558 |  | 0.356 | 0.364 |
| Bst | 0.407 | 0.397 | 0.405 | 0.397 | 0.407 | 0.406 | 0.404 | 0.338 | 0.37 | 0.377 | 0.356 |  | 0.881 |
| Bca | 0.408 | 0.397 | 0.397 | 0.398 | 0.399 | 0.406 | 0.404 | 0.339 | 0.377 | 0.376 | 0.364 | 0.881 |  |

| B. | Sequence identities over polymerase sub domain only (corresponding to amino acids 420-834 of Z05) | | | | | | | | | | | | |
|---|---|---|---|---|---|---|---|---|---|---|---|---|---|
| Name | Z05 | Taq | Tfi | Tfl | Sps17 | Tth | Tca | Dra | Tma | Tne | Taf | Bst | Bca |
| Z05 |  | 0.901 | 0.845 | 0.891 | 0.845 | 0.975 | 0.973 | 0.563 | 0.483 | 0.478 | 0.44 | 0.498 | 0.49 |
| Taq | 0.901 |  | 0.879 | 0.901 | 0.877 | 0.906 | 0.901 | 0.561 | 0.488 | 0.473 | 0.44 | 0.503 | 0.495 |
| Tfi | 0.845 | 0.879 |  | 0.857 | 0.997 | 0.853 | 0.853 | 0.566 | 0.495 | 0.49 | 0.449 | 0.512 | 0.49 |
| Tfl | 0.891 | 0.901 | 0.857 |  | 0.855 | 0.889 | 0.889 | 0.571 | 0.492 | 0.48 | 0.444 | 0.494 | 0.485 |
| Sps17 | 0.845 | 0.877 | 0.997 | 0.855 |  | 0.853 | 0.853 | 0.566 | 0.495 | 0.49 | 0.449 | 0.512 | 0.49 |
| Tth | 0.975 | 0.906 | 0.853 | 0.889 | 0.853 |  | 0.99 | 0.563 | 0.478 | 0.473 | 0.437 | 0.496 | 0.488 |
| Tca | 0.973 | 0.901 | 0.853 | 0.889 | 0.853 | 0.99 |  | 0.563 | 0.478 | 0.473 | 0.437 | 0.496 | 0.488 |
| Dra | 0.563 | 0.561 | 0.566 | 0.571 | 0.566 | 0.563 | 0.563 |  | 0.45 | 0.448 | 0.426 | 0.474 | 0.454 |
| Tma | 0.483 | 0.488 | 0.495 | 0.492 | 0.495 | 0.478 | 0.478 | 0.45 |  | 0.883 | 0.622 | 0.474 | 0.475 |
| Tne | 0.478 | 0.473 | 0.49 | 0.48 | 0.49 | 0.473 | 0.473 | 0.448 | 0.883 |  | 0.615 | 0.476 | 0.473 |
| Taf | 0.44 | 0.44 | 0.449 | 0.444 | 0.449 | 0.437 | 0.437 | 0.426 | 0.622 | 0.615 |  | 0.46 | 0.473 |
| Bst | 0.498 | 0.503 | 0.512 | 0.494 | 0.512 | 0.496 | 0.496 | 0.474 | 0.474 | 0.476 | 0.46 |  | 0.898 |
| Bca | 0.49 | 0.495 | 0.49 | 0.485 | 0.49 | 0.488 | 0.488 | 0.454 | 0.475 | 0.473 | 0.473 | 0.898 |  |

*Fig. 2*

| A. Sequence identities over the entire polymerase I enzyme (corresponding to amino acids 1-834 of Z05) | | | | | | | |
|---|---|---|---|---|---|---|---|
| Name | Z05 | Tth | Tfi | Tfl | Tca | Taq | Sps17 |
| Z05 |  | 0.962 | 0.833 | 0.859 | 0.958 | 0.864 | 0.839 |
| Tth | 0.962 |  | 0.829 | 0.853 | 0.989 | 0.872 | 0.835 |
| Tfi | 0.833 | 0.829 |  | 0.82 | 0.824 | 0.831 | 0.991 |
| Tfl | 0.859 | 0.853 | 0.82 |  | 0.848 | 0.854 | 0.824 |
| Tca | 0.958 | 0.989 | 0.824 | 0.848 |  | 0.864 | 0.83 |
| Taq | 0.864 | 0.872 | 0.831 | 0.854 | 0.864 |  | 0.836 |
| Sps17 | 0.839 | 0.835 | 0.991 | 0.824 | 0.83 | 0.836 |  |

| B. Sequence identities over polymerase sub domain only (corresponding to amino acids 420-834 of Z05) | | | | | | | |
|---|---|---|---|---|---|---|---|
| Name | Z05 | Tth | Tfi | Tfl | Tca | Taq | Sps17 |
| Z05 |  | 0.975 | 0.845 | 0.891 | 0.973 | 0.901 | 0.845 |
| Tth | 0.975 |  | 0.853 | 0.889 | 0.99 | 0.906 | 0.853 |
| Tfi | 0.845 | 0.853 |  | 0.857 | 0.853 | 0.879 | 0.997 |
| Tfl | 0.891 | 0.889 | 0.857 |  | 0.889 | 0.901 | 0.855 |
| Tca | 0.973 | 0.99 | 0.853 | 0.889 |  | 0.901 | 0.853 |
| Taq | 0.901 | 0.906 | 0.879 | 0.901 | 0.901 |  | 0.877 |
| Sps17 | 0.845 | 0.853 | 0.997 | 0.855 | 0.853 | 0.877 |  |

*Fig. 4A*
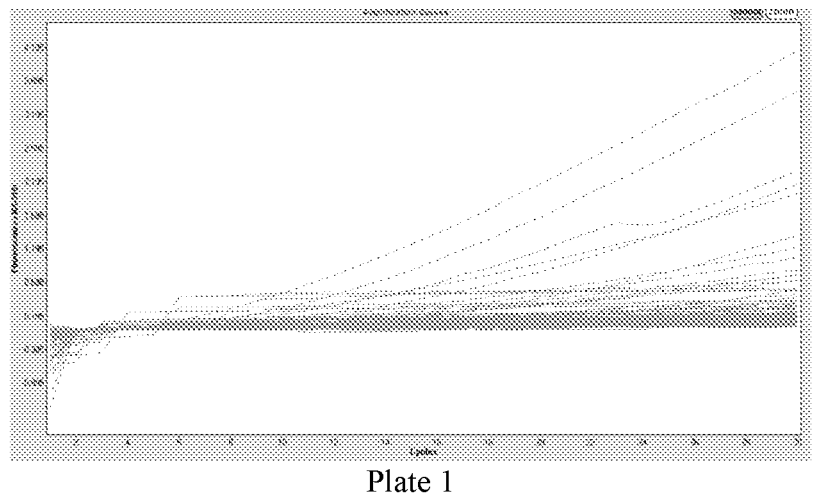
Plate 1
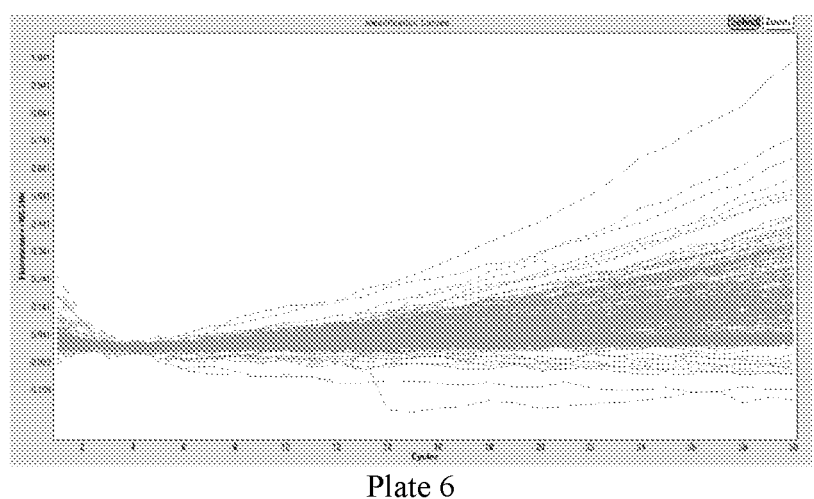
Plate 6

Fig. 4B
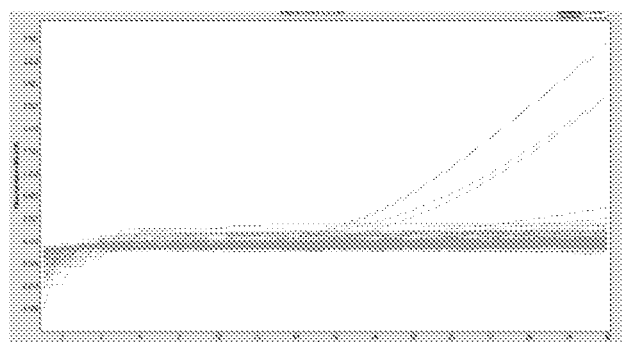
Plate 2
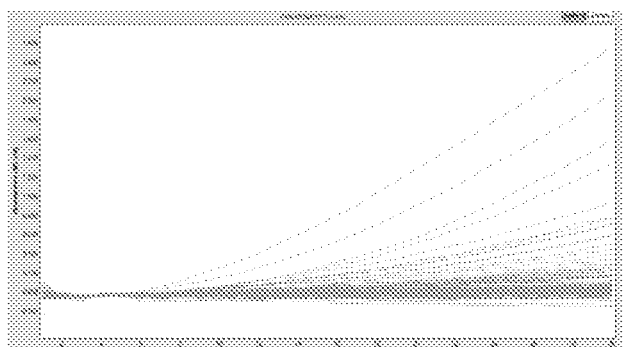
Plate 3
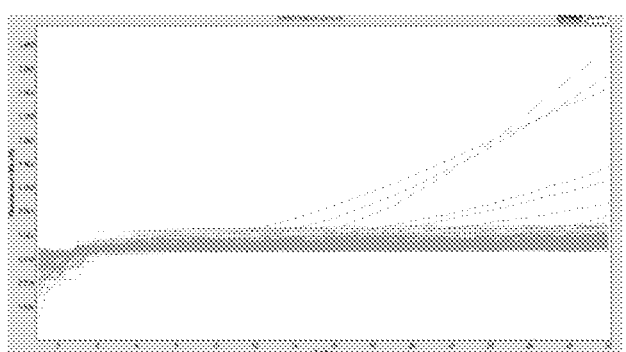
Plate 4
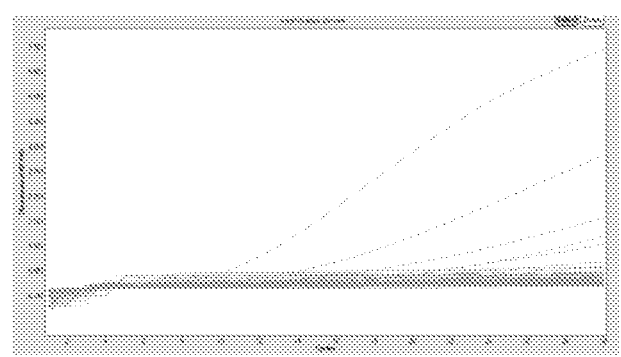
Plate 5

MUTANT DNA POLYMERASE(S) WITH IMPROVED STRAND DISPLACEMENT ABILITY

PRIORITY INFORMATION

This patent application claims priority to U.S. Provisional Patent Application No. 62/730,908, filed Sep. 13, 2018, the contents of which are hereby incorporated by reference in its entirety for all purposes. The Sequence Listing submitted as an XML file named "P34971-US-2_Seq_Listing", having a size of 87,454 bytes and created on Dec. 20, 2023, is hereby incorporated by reference in its entirety for all purposes.

FIELD OF THE INVENTION

The present invention provides DNA polymerases with improved activities, including increased 5'-3' strand displacement activity and substantially reduced 5'-3' exo/endo nuclease activity, as well as use of such polymerases in various applications, including nucleic acid polynucleotide extension and amplification.

BACKGROUND OF THE INVENTION

DNA polymerases are responsible for the replication and maintenance of the genome, a role that is central to accurately transmitting genetic information from generation to generation. DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. In vivo, DNA polymerases participate in a spectrum of DNA synthetic processes including DNA replication, DNA repair, recombination, and gene amplification. During each DNA synthetic process, the DNA template is copied once or at most a few times to produce identical replicas. In contrast, in vitro, DNA replication can be repeated many times such as, for example, during polymerase chain reaction (see, e.g., U.S. Pat. No. 4,683,202 to Mullis).

In the initial studies with polymerase chain reaction (PCR), the DNA polymerase was added at the start of each round of DNA replication (see U.S. Pat. No. 4,683,202, supra). Subsequently, it was determined that thermostable DNA polymerases could be obtained from bacteria that grow at elevated temperatures, and that these enzymes need to be added only once (see U.S. Pat. No. 4,889,818 to Gelfand and U.S. Pat. No. 4,965,188 to Mullis). At the elevated temperatures used during PCR, these enzymes are not irreversibly inactivated. As a result, one can carry out repetitive cycles of polymerase chain reactions without adding fresh enzymes at the start of each synthetic addition process. DNA polymerases, particularly thermostable polymerases, are the key to a large number of techniques in recombinant DNA studies and in medical diagnosis of disease. For diagnostic applications in particular, a target nucleic acid sequence may be only a small portion of the DNA or RNA in question, so it may be difficult to detect the presence of a target nucleic acid sequence without amplification.

The overall folding pattern of DNA polymerases resembles the human right hand and contains three distinct subdomains of palm, fingers, and thumb. (See Beese et al., *Science* 260:352-355, 1993); Patel et al., *Biochemistry* 34:5351-5363, 1995). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a mean deviation of about one A amongst mammalian pol α and prokaryotic pol I family DNA polymerases (Wang et al., *Cell* 89:1087-1099, 1997). Motif A begins structurally at an antiparallel β-strand containing predominantly hydrophobic residues and continues to an α-helix. The primary amino acid sequence of DNA polymerase active sites is exceptionally conserved. In the case of motif A, for example, the sequence DYSQIELR (SEQ ID NO:22) is retained in polymerases from organisms separated by many millions of years of evolution, including, e.g., *Thermus aquaticus*, *Chlamydia trachomatis*, and *Escherichia coli*.

In addition to being well-conserved, the active site of DNA polymerases has also been shown to be relatively mutable, capable of accommodating certain amino acid substitutions without reducing DNA polymerase activity significantly. (See, e.g., U.S. Pat. No. 6,602,695 to Patel et al.). Such mutant DNA polymerases can offer various selective advantages in, e.g., diagnostic and research applications comprising nucleic acid synthesis reactions.

Strand displacement refers to the ability of a polymerase to displace, rather than degrade, downstream DNA encountered during synthesis of DNA. During strand displacement replication, only one DNA strand is replicated at once. Strand displacement synthesis releases a single stranded DNA, which is then copied into double-stranded DNA. Many thermostable DNA polymerases exhibit rapid and processive primer extension DNA synthesis, but inefficient strand displacement DNA synthesis. This disclosure provides thermostable DNA polymerases with improved strand displacement, activity at elevated temperatures that result in improved 5'-3' strand displacement activity and substantially reduced 5'-3' exo/endo nuclease activity.

BRIEF SUMMARY OF THE INVENTION

Provided herein are thermostable DNA Polymerases with improved strand displacement activity at elevated temperatures when other DNA polymerases with prominent strand displacement activities like Phi 29 DNA Polymerase or Bst DNA Polyrnerase fail to function. This disclosure describes mutations in the polymerase domain of DNA polymerases that result in improved 5'-3' strand displacement activity and substantially reduced exonuclease and/or endonuclease activity. In some embodiments the DNA polymerase has decreased 5'-3' exonuclease and/or endonuclease activity. The mutations described herein provide unexpected advantages that could not have been predicted based on existing three dimensional structures of closely related DNA polymerases, and it was not predictable even in retrospect that the mutant polymerases described herein would demonstrate enhanced strand displacement activity.

In one aspect, provided herein are DNA polymerases having improved activities, including increased 5'-3' strand displacement activity and substantially reduced 5'-3' exo/endo nuclease activity, relative to a corresponding, unmodified control polymerase, and methods of making and using such DNA polymerases. In some embodiments, the improved DNA polymerase has increased 5'-3' strand displacement activity as compared with a control DNA polymerase. In some embodiments, the improved DNA polymerase has substantially reduced 5'-3' exo/endo nuclease activity as compared with a control DNA polymerase. In some embodiments, the control DNA polymerase comprises the amino acid sequence of SEQ ID NO:1. In some embodiments, the control DNA polymerase comprises the amino acid sequence of SEQ ID NO:1, except the control DNA polymerase has a mutation at the amino acid corresponding to position 46 of SEQ ID NO:1. In some embodiments, the control DNA polymerase comprises a Glycine (Gly/G) to Glutamic acid (Glu/E) mutation at the amino acid corresponding to position 46 of SEQ ID NO:1. The G46E mutation impairs 5'-3' exonuclease and endonuclease activity, which are undesirable for a strand-displacement enzyme. In some embodiments, the control DNA polymerase comprises the amino acid sequence of SEQ ID NO:40. In some embodiments, the control DNA polymerase is encoded by the nucleic acid sequence of SEQ ID NO:41. In some embodiments, the improved or mutant DNA polymerases described herein are encoded by a nucleic acid sequence having at least 80%, 85%, 90%, 91%, 92%, 93%. 94%, 95%, 96%, 97%, 98%, or 99% to SEQ ID NO:41. In some embodiments, the control DNA polymerase comprises the amino acid sequence of SEQ ID NO:42.

In some embodiments, the improved DNA polymerase comprises one or more mutations, or a combination of mutations, at positions corresponding to the following positions of SEQ ID NO:1 or SEQ ID NO:40:
686, 693, 516, 633, 415, 420, 636, 752, 768, 525, 694, 491, 516, 515, 666, 402, 555, 582, 737, 759, 521, 546, 668, 456, 507, 571, 652, 832, 498, 524, 598, 616, 444, 498, 660, 673, 493, 511, 648, 749 and 635.

In some embodiments, the improved DNA polymerase comprises one or more mutations, or a combination of mutations, at positions corresponding to the following positions of SEQ ID NO:1 or SEQ ID NO:40:
I686V, A693V, T516I, V633I, Q415H, E420D, E636G, N752S, V768M, R525G, F694S, Q491H, T516S, S515F, T666M, E402V, V555A, N582D A737T, A759T, L521Q, T546A, N668S, A456T, K507M, T571A, S652F, A832V, D498E, L524V, R598G, M616I, A444T, M660K, Y673N, E493D, T511S, M648I, M749L and/or Q635K.

In some embodiments, the improved DNA polymerase comprises an amino acid sequence that is substantially identical (e.g., at least about 60%, 65%, 70%, 75%, 80%, 85%, 90%, or 95% identical) to SEQ ID NO:1, wherein the amino acid sequence of the DNA polymerase comprises one or more mutations, or a combination of mutations, at positions corresponding to the following positions of SEQ ID NO:1 or SEQ ID NO:40:
686, 693, 516, 633, 415, 420, 636, 752, 768, 525, 694, 491, 516, 515, 666, 402, 555, 582, 737, 759, 521, 546, 668, 456, 507, 571, 652, 832, 498, 524, 598, 616, 444, 498, 660, 673, 493, 511, 648, 749 and 635.

In some embodiments, the improved DNA polymerase comprises an amino acid sequence that is substantially identical (e.g., at least about 60%, 65%, 70%, 75%, 80%, 85%, 90%, or 95% identical) to SEQ ID NO:1, wherein the amino acid sequence of the DNA polymerase comprises one or more mutations, or a combination of mutations, at positions corresponding to the following positions of SEQ ID NO:1 or SEQ ID NO:40:
I686, A693, T516, V633, Q415, E420, E636, N752, V768, R525, F694, Q491, T516, S515, T666, E402, V555, N582, A737, A759, L521, T546, N668, A456, K507, T571, S652, A832, D498, L524, R598, M616, A444, D498, M660, Y673, E493, T511, M648, M749 and/or Q635.

In some embodiments, the improved DNA polymerase comprises an amino acid sequence that is substantially identical (e.g., at least about 60%, 65%, 70%, 75%, 80%, 85%, 90%, or 95% identical) to SEQ ID NO:1, wherein:

i. the amino acid of the DNA polymerase corresponding to position 686 of SEQ ID NO:1 is any amino acid other than I;

ii. the amino acid of the DNA polymerase corresponding to position 693 of SEQ ID NO:1 is any amino acid other than A;

iii. the amino acid of the DNA polymerase corresponding to position 516 of SEQ ID NO:1 is any amino acid other than T;

iv. the amino acid of the DNA polymerase corresponding to position 633 of SEQ ID NO:1 is any amino acid other than V;

v. the amino acid of the DNA polymerase corresponding to position 415 of SEQ ID NO:1 is any amino acid other than Q;

vi. the amino acid of the DNA polymerase corresponding to position 420 of SEQ ID NO:1 is any amino acid other than E;

vii. the amino acid of the DNA polymerase corresponding to position 636 of SEQ ID NO:1 is any amino acid other than E;

viii. the amino acid of the DNA polymerase corresponding to position 752 of SEQ ID NO:1 is any amino acid other than N;

ix. the amino acid of the DNA polymerase corresponding to position 768 of SEQ ID NO:1 is any amino acid other than V;

x. the amino acid of the DNA polymerase corresponding to position 525 of SEQ ID NO:1 is any amino acid other than R;

xi. the amino acid of the DNA polymerase corresponding to position 694 of SEQ ID NO:1 is any amino acid other than F;

xii. the amino acid of the DNA polymerase corresponding to position 491 of SEQ ID NO:1 is any amino acid other than Q;

xiii. the amino acid of the DNA polymerase corresponding to position 516 of SEQ ID NO:1 is any amino acid other than T;

xiv. the amino acid of the DNA polymerase corresponding to position 515 of SEQ ID NO:1 is any amino acid other than S;

xv. the amino acid of the DNA polymerase corresponding to position 666 of SEQ ID NO:1 is any amino acid other than T;

xvi. the amino acid of the DNA polymerase corresponding to position 402 of SEQ ID NO:1 is any amino acid other than E;

xvii. the amino acid of the DNA polymerase corresponding to position 555 of SEQ ID NO:1 is any amino acid other than V;

xviii. the amino acid of the DNA polymerase corresponding to position 582 of SEQ ID NO:1 is any amino acid other than N;

xix. the amino acid of the DNA polymerase corresponding to position 737 of SEQ ID NO:1 is any amino acid other than A;

xx. the amino acid of the DNA polymerase corresponding to position 759 of SEQ ID NO:1 is any amino acid other than A;

xxi. the amino acid of the DNA polymerase corresponding to position 521 of SEQ ID NO:1 is any amino acid other than L;

xxii. the amino acid of the DNA polymerase corresponding to position 546 of SEQ ID NO:1 is any amino acid other than T;

xxiii. the amino acid of the DNA polymerase corresponding to position 668 of SEQ ID NO:1 is any amino acid other than N;

xxiv. the amino acid of the DNA polymerase corresponding to position 456 of SEQ ID NO:1 is any amino acid other than A;

xxv. the amino acid of the DNA polymerase corresponding to position 507 of SEQ ID NO:1 is any amino acid other than K;

xxvi. the amino acid of the DNA polymerase corresponding to position 571 of SEQ ID NO:1 is any amino acid other than T;

xxvii. the amino acid of the DNA polymerase corresponding to position 652 of SEQ ID NO:1 is any amino acid other than S;

xxviii. the amino acid of the DNA polymerase corresponding to position 832 of SEQ ID NO:1 is any amino acid other than A;

xxix. the amino acid of the DNA polymerase corresponding to position 498 of SEQ ID NO:1 is any amino acid other than D;

xxx. the amino acid of the DNA polymerase corresponding to position 524 of SEQ ID NO:1 is any amino acid other than L;

xxxi. the amino acid of the DNA polymerase corresponding to position 598 of SEQ ID NO:1 is any amino acid other than R;

xxxii. the amino acid of the DNA polymerase corresponding to position 616 of SEQ ID NO:1 is any amino acid other than M;

xxxiii. the amino acid of the DNA polymerase corresponding to position 444 of SEQ ID NO:1 is any amino acid other than A;

xxxiv. the amino acid of the DNA polymerase corresponding to position 660 of SEQ ID NO:1 is any amino acid other than M;

xxxv. the amino acid of the DNA polymerase corresponding to position 673 of SEQ ID NO:1 is any amino acid other than Y;

xxxvi. the amino acid of the DNA polymerase corresponding to position 493 of SEQ ID NO:1 is any amino acid other than E;

xxxvii. the amino acid of the DNA polymerase corresponding to position 511 of SEQ ID NO:1 is any amino acid other than T;

xxxviii. the amino acid of the DNA polymerase corresponding to position 648 of SEQ ID NO:1 is any amino acid other than M;

xxxix. the amino acid of the DNA polymerase corresponding to position 749 of SEQ ID NO:1 is any amino acid other than M; and/or xl. the amino acid of the DNA polymerase corresponding to position 635 of SEQ ID NO:1 is any amino acid other than Q.

In some embodiments, the improved DNA polymerase comprises an amino acid sequence that is substantially identical (e.g., at least about 60%, 65%, 70%, 75%, 80%, 85%, 90%, or 95% identical) to SEQ ID NO:1, wherein:

i. the amino acid of the DNA polymerase corresponding to position 686 of SEQ ID NO:1 is V;

ii. the amino acid of the DNA polymerase corresponding to position 693 of SEQ ID NO:1 is V;

iii. the amino acid of the DNA polymerase corresponding to position 516 of SEQ ID NO:1 is I;

iv. the amino acid of the DNA polymerase corresponding to position 633 of SEQ ID NO:1 is I;

v. the amino acid of the DNA polymerase corresponding to position 415 of SEQ ID NO:1 is H;

vi. the amino acid of the DNA polymerase corresponding to position 420 of SEQ ID NO:1 is D;

vii. the amino acid of the DNA polymerase corresponding to position 636 of SEQ ID NO:1 is G;

viii. the amino acid of the DNA polymerase corresponding to position 752 of SEQ ID NO:1 is S;

ix. the amino acid of the DNA polymerase corresponding to position 768 of SEQ ID NO:1 is M;

x. the amino acid of the DNA polymerase corresponding to position 525 of SEQ ID NO:1 is G;

xi. the amino acid of the DNA polymerase corresponding to position 694 of SEQ ID NO:1 is S;

xii. the amino acid of the DNA polymerase corresponding to position 491 of SEQ ID NO:1 is H;

xiii. the amino acid of the DNA polymerase corresponding to position 516 of SEQ ID NO:1 is S;

xiv. the amino acid of the DNA polymerase corresponding to position 515 of SEQ ID NO:1 is F;

xv. the amino acid of the DNA polymerase corresponding to position 666 of SEQ ID NO:1 is M;

xvi. the amino acid of the DNA polymerase corresponding to position 402 of SEQ ID NO:1 is V;

xvii. the amino acid of the DNA polymerase corresponding to position 555 of SEQ ID NO:1 is A;

xviii. the amino acid of the DNA polymerase corresponding to position 582 of SEQ ID NO:1 is D;

xix. the amino acid of the DNA polymerase corresponding to position 737 of SEQ ID NO:1 is T;

xx. the amino acid of the DNA polymerase corresponding to position 759 of SEQ ID NO:1 is T;

xxi. the amino acid of the DNA polymerase corresponding to position 521 of SEQ ID NO:1 is Q;

xxii. the amino acid of the DNA polymerase corresponding to position 546 of SEQ ID NO:1 is A;

xxiii. the amino acid of the DNA polymerase corresponding to position 668 of SEQ ID NO:1 is S;

xxiv. the amino acid of the DNA polymerase corresponding to position 456 of SEQ ID NO:1 is T;

xxv. the amino acid of the DNA polymerase corresponding to position 507 of SEQ ID NO:1 is M;

xxvi. the amino acid of the DNA polymerase corresponding to position 571 of SEQ ID NO:1 is A;

xxvii. the amino acid of the DNA polymerase corresponding to position 652 of SEQ ID NO:1 is F xxviii. the amino acid of the DNA polymerase corresponding to position 832 of SEQ ID NO:1 is V;

xxix. the amino acid of the DNA polymerase corresponding to position 498 of SEQ ID NO:1 is E;

xxx. the amino acid of the DNA polymerase corresponding to position 524 of SEQ ID NO:1 is V;

xxxi. the amino acid of the DNA polymerase corresponding to position 598 of SEQ ID NO:1 is G;

xxxii. the amino acid of the DNA polymerase corresponding to position 616 of SEQ ID NO:1 is I;

xxxiii. the amino acid of the DNA polymerase corresponding to position 444 of SEQ ID NO:1 is T;

xxxiv. the amino acid of the DNA polymerase corresponding to position 660 of SEQ ID NO:1 is K;

xxxv. the amino acid of the DNA polymerase corresponding to position 673 of SEQ ID NO:1 is any amino acid other than Y;

xxxvi. the amino acid of the DNA polymerase corresponding to position 493 of SEQ ID NO:1 is D;

xxxvii. the amino acid of the DNA polymerase corresponding to position 511 of SEQ ID NO:1 is S;

xxxviii. the amino acid of the DNA polymerase corresponding to position 648 of SEQ ID NO:1 is I;
xxxix. the amino acid of the DNA polymerase corresponding to position 749 of SEQ ID NO:1 is L; and/or
xl. the amino acid of the DNA polymerase corresponding to position 635 of SEQ ID NO:1 is K.

In some embodiments, the improved DNA polymerase comprises an amino acid sequence that is substantially identical (e.g., at least about 60%, 65%, 70%, 75%, 80%, 85%, 90%, or 95% identical) to SEQ ID NO:1, wherein the amino acid sequence of the DNA polymerase comprises one or more mutations, or a combination of mutations, at positions corresponding to the following positions of SEQ ID NO:1 or SEQ ID NO:40:

I686V, A693V, T516I, V633I, Q415H, E420D, E636G, N752S, V768M, R525G, F694S, Q491H, T516S, S515F, T666M, E402V, V555A, N582D A737T, A759T, L521Q, T546A, N668S, A456T, K507M, T571A, S652F, S515F, A832V, D498E, L524V, R598G, M616I, A444T, D498E, M660K, Y673N, E493D, T511S, M648I, M749L and/or Q635K.

In some embodiments, the improved DNA polymerase comprises one or more mutations, or a combination of mutations, at the following positions of SEQ ID NO:1 or SEQ ID NO:40:

686, 693, 516, 633, 415, 420, 636, 752, 768, 525, 694, 491, 516, 515, 666, 402, 555, 582, 737, 759, 521, 546, 668, 456, 507, 571, 652, 515, 832, 498, 524, 598, 616, 444, 498, 660, 673, 493, 511, 648, 749 and 635.

In some embodiments, the improved DNA polymerase comprises one or more mutations, or a combination of mutations, at the following positions of SEQ ID NO:1 or SEQ ID NO:40:

I686V, A693V, T516I, V633I, Q415H, E420D, E636G, N752S, V768M, R525G, F694S, Q491H, T516S, S515F, T666M, E402V, V555A, N582D A737T, A759T, L521Q, T546A, N668S, A456T, K507M, T571A, S652F, S515F, A832V, D498E, L524V, R598G, M616I, A444T, M660K, Y673N, E493D, T511S, M648I, M749L and/or Q635K.

In some embodiments, the amino acid sequence of the DNA polymerase comprises single and/or combinations of mutations at positions corresponding to the following positions of SEQ ID NO:1 or SEQ ID NO:40:
i. I686V and A693V;
ii. T516I and V633I;
iii. Q415H, E420D, E636G, N752S, and V768M;
iv. R525G and F694S;
v. Q491H and T516S;
vi. S515F and T666M;
vii. E402V, V555A and N582D;
viii. A737T and A759T;
ix. L521Q and T546A;
x. N668S;
xi. A456T;
xii. K507M, T571A and S652F;
xiii. S515F and A832V;
xiv. D498E, L524V, R598G and M616I;
xv. A444T, D498E, M660K and Y673N;
xvi. E493D, T511S, M648I and M749L; and/or
xvii. Q635K.

In some embodiments, the mutations are located in the following "hot spots" or stretches in the primary amino acid sequence corresponding to amino acids 515-516, 521-525, 633-636, 666-668, and 693-694 of SEQ ID NO:1 or SEQ ID NO:40.

In some embodiments, the improved DNA polymerase further comprises an amino acid sequence that is substantially identical (e.g., at least about 60%, 65%, 70%, 75%, 80%, 85%, 90%, or 95% identical) to SEQ ID NO:40, wherein the amino acid of the DNA polymerase corresponding to position 46 of SEQ ID NO:40 is Glu (E).

In some embodiments, the improved DNA polymerase further comprises an amino acid sequence that is substantially identical (e.g., at least about 60%, 65%, 70%, 75%, 80%, 85%, 90%, or 95% identical) to SEQ ID NO:1, wherein the amino acid of the DNA polymerase corresponding to position 580 of SEQ ID NO:1 is any amino acid other than D or E. In some embodiments, the amino acid of the DNA polymerase corresponding to position 580 of SEQ ID NO:1 is any amino acid other than D. In some embodiments, the amino acid of the DNA polymerase corresponding to position 580 of SEQ ID NO:1 is selected from the group consisting of L, G, T, Q, A, S, N, R, and K. In some embodiments, the amino acid of the DNA polymerase corresponding to position 580 of SEQ ID NO:1 is G.

In some embodiments, the improved DNA polymerase further comprises an amino acid sequence that is substantially identical (e.g., at least about 60%, 65%, 70%, 75%, 80%, 85%, 90%, or 95% identical) to SEQ ID NO:1, wherein the amino acid of the DNA polymerase corresponding to position 709 of SEQ ID NO:1 is any amino acid other than I. In some embodiments, the amino acid of the DNA polymerase corresponding to position 709 of SEQ ID NO:1 is selected from the group consisting of K, R, S, G, and A. In some embodiments, the amino acid of the DNA polymerase corresponding to position 709 of SEQ ID NO:1 is K.

Various DNA polymerases are amenable to mutation according to the present invention. Particularly suitable are thermostable polymerases, including wild-type or naturally occurring thermostable polymerases from various species of thermophilic bacteria, as well as synthetic thermostable polymerases derived from such wild-type or naturally occurring enzymes by amino acid substitution, insertion, or deletion, or other modification. Exemplary unmodified forms of polymerase include, e.g., CS5, CS6 or Z05 DNA polymerase, or a functional DNA polymerase having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity thereto. Other unmodified polymerases include, e.g., DNA polymerases from any of the following species of thermophilic bacteria (or a functional DNA polymerase having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to such a polymerase): *Thermotoga maritima; Thermus aquaticus; Thermus thermophilus; Thermus flavus; Thermus filiformis; Thermus* sp. sps17; *Thermus* sp. Z05; *Thermotoga neopolitana; Thermosipho africanus; Thermus caldophilus, Deinococcus radiodurans, Bacillus stearothermophilus* or *Bacillus caldotenax*. Suitable polymerases also include those having reverse transcriptase (RT) activity and/or the ability to incorporate unconventional nucleotides, such as ribonucleotides or other 2'-modified nucleotides.

While thermostable DNA polymerases possessing efficient reverse transcription activity are particularly suited for performing RT-PCR, especially single enzyme RT-PCR, thermoactive, but not thermostable DNA polymerases possessing efficient reverse transcription activity also are amenable to mutation according to the present invention. For example, the attributes of increased reverse transcriptase efficiency, mismatch tolerance, extension rate, and/or tolerance of RT inhibitors are useful for the RT step in an RT-PCR and this step does not need to be performed at temperatures that would inactivate a thermoactive but not thermostable DNA polymerase. Following the RT step, a thermostable DNA polymerase could either be added or it could already be included in the reaction mixture to perform the PCR amplification step. For example, the improved DNA polymerase described herein can be combined with a second thermostable DNA polymerase prior to the RT step in a buffer suitable for extension and amplification of RNA and DNA templates, as described in the Examples. Examples of suitable thermostable DNA polymerases are described in U.S. Pat. No. 4,889,818 to Gelfand et al., and U.S. Pat. Nos. 5,773,258 and 5,677,152 to Birch et al., which are expressly incorporated by reference herein in their entirety. In some embodiments, the second thermostable DNA polymerase is AmpliTaq® DNA polymerase (Deoxynucleoside triphosphate: DNA Deoxynucleotidyltransferase, E.C.2.7.7.7). In some embodiments, the second thermostable DNA polymerase is a reversibly inactivated thermostable polymerase, as described below. In one embodiment, the reversibly inactivated thermostable polymerase is AmpliTaq Gold® DNA polymerase (Roche Applied Science, Indianapolis, IN, USA). This second methodology would especially benefit by using a chemically modified thermostable DNA polymerase (or other HotStart technology to inactivate the thermostable DNA polymerase) so that it would not be fully active during the RT step. An example of a thermoactive but not thermostable DNA polymerase possessing efficient reverse transcription activity is the DNA polymerase from *Carboxydothermus hydrogenoformans* (Chy; SEQ ID NO:39). See, e.g., U.S. Pat. Nos. 6,468,775 and 6,399,320.

In some embodiments, the DNA polymerase has at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polymerase selected from the group consisting of:
  (a) a *Thermus* sp. Z05 DNA polymerase (Z05) (SEQ ID NO:1);
  (b) a *Thermus aquaticus* DNA polymerase (Taq) (SEQ ID NO:2);
  (c) a *Thermus filiformis* DNA polymerase (Tfi) (SEQ ID NO:3);
  (d) a *Thermus flavus* DNA polymerase (Tfl) (SEQ ID NO:4);
  (e) a *Thermus* sp. sps17 DNA polymerase (Sps17) (SEQ ID NO:5);
  (f) a *Thermus thermophilus* DNA polymerase (Tth) (SEQ ID NO:6); and
  (g) a *Thermus caldophilus* DNA polymerase (Tca) (SEQ ID NO:7)
  (h) *Carboxydothermus* hydrogenoformans DNA polymerase (Chy) (SEQ ID NO:39)

In some embodiments, the DNA polymerase is a *Thermotoga* DNA polymerase. For example, in some embodiments, the DNA polymerase has at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polymerase selected from the group consisting of:
  (a) a *Thermotoga maritima* DNA polymerase (Tma) (SEQ ID NO:34);
  (b) a *Thermotoga neopolitana* DNA polymerase (Tne) (SEQ ID NO:35);

In some embodiments, the DNA polymerase has at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to SEQ ID NO:1, SEQ ID NO:40, or SEQ ID NO:42. In some embodiments, the DNA polymerase is a Z05 DNA polymerase further comprising a substitution at position 580, and the amino acid at position 580 is any amino acid other than D or E. In some embodiments, the DNA polymerase is a Z05 DNA polymerase, and the amino acid at position 580 is any amino acid other than D. In some embodiments, the DNA polymerase is a Z05 DNA polymerase, and the amino acid at position 580 is selected from the group consisting of L, G, T, Q, A, S, N, R, and K. In some embodiments, the DNA polymerase is a Z05 DNA polymerase, and the amino acid at position 580 is G. In some embodiments, the DNA polymerase is a Z05 DNA polymerase further comprising a substitution at position 709, and the amino acid at position 709 is any amino acid other than I. In some embodiments, the DNA polymerase is a Z05 DNA polymerase, and the amino acid at position 709 is selected from the group consisting of K, R, S, G, and A. In some embodiments, the DNA polymerase is a Z05 DNA polymerase, and the amino acid at position 709 is K.

In some embodiments, the control DNA polymerase is a Z05, Z05 D580G, or Z05 D580G I709K polymerase. In some embodiments, the control DNA polymerase is a C21 or C21 G46E polymerase (SEQ ID NO: 40). In some embodiments, the control DNA polymerase comprises the amino acid sequence of SEQ ID NO:1, SEQ ID NO: 40, or SEQ ID NO: 42.

The mutant or improved polymerases can include other, non-substitutional modifications. One such modification is a thermally reversible covalent modification that inactivates the enzyme, but which is reversed to activate the enzyme upon incubation at an elevated temperature, such as a temperature typically used for polynucleotide extension. Exemplary reagents for such thermally reversible modifications are described in U.S. Pat. Nos. 5,773,258 and 5,677,152 to Birch et al., which are expressly incorporated by reference herein in their entirety.

In various other aspects, the present disclosure provides a recombinant nucleic acid encoding a mutant or improved DNA polymerase as described herein, a vector comprising the recombinant nucleic acid, and a host cell transformed with the vector. In certain embodiments, the vector is an expression vector. Host cells comprising such expression vectors are useful in methods of the invention for producing the mutant or improved polymerase by culturing the host cells under conditions suitable for expression of the recombinant nucleic acid. The polymerases of the invention may be contained in reaction mixtures and/or kits. The embodiments of the recombinant nucleic acids, host cells, vectors, expression vectors, reaction mixtures and kits are as described above and herein.

In yet another aspect, a method for conducting polynucleotide extension is provided. The method generally includes contacting a DNA polymerase described herein having increased strand displacement activity and substantially reduced 5'-3'exonuclease/endonuclease activity with a primer, a polynucleotide template, and nucleoside triphosphates under conditions suitable for extension of the primer, thereby producing an extended primer. The polynucleotide template can be, for example, an RNA or DNA template. The nucleotide triphosphates can include unconventional nucleotides such as, e.g., ribonucleotides and/or labeled nucleotides. Further, the primer and/or template can include one or more nucleotide analogs. In some variations, the polynucleotide extension method is a method for polynucleotide amplification that includes contacting the mutant or improved DNA polymerase with a primer pair, the polynucleotide template, and the nucleoside triphosphates under conditions suitable for amplification of the polynucleotide. The polynucleotide extension reaction can be, e.g., PCR, isothermal extension, or sequencing (e.g., 454 sequencing reaction). The polynucleotide template can be from any type of biological sample.

In some embodiments, the primer extension method comprises a strand displacement reaction, a polymerase chain reaction (PCR), an isothermal amplification, or an amplification reaction selected from loop-mediated amplification (LAMP), cross-priming amplification (CSA) and Polymerase Chain Displacement Reaction (PCDR). In some embodiments, the conditions suitable for extension of the primer include elevated temperature.

Optionally, the primer extension reaction comprises an actual or potential inhibitor of a reference or unmodified polymerase. The inhibitor can inhibit the nucleic acid extension rate and/or the strand displacement activity of a reference or unmodified (control) polymerase. In some embodiments, the inhibitor is hemoglobin, or a degradation product thereof. For example, in some embodiments, the hemoglobin degradation product is a heme breakdown product, such as hemin, hematoporphyrin, or bilirubin. In some embodiments, the inhibitor is an iron-chelator or a purple pigment. In other embodiments, the inhibitor is heparin or melanin. In certain embodiments, the inhibitor is an intercalating dye. In some embodiments, the intercalating dye is [2-[N-bis-(3-dimethylaminopropyl)-amino]-4-[2,3-dihydro-3-methyl-(benzo-1,3-thiazol-2-yl)-methylidene]-1-phenyl-quinolinium]+. In some embodiments, the intercalating dye is [2-[N-(3-dimethylaminopropyl)-N-propylamino]-4-[2,3-dihydro-3-methyl-(benzo-1,3-thiazol-2-yl)-methylidene]-1-phenyl-quinolinium]+. In some embodiments, the intercalating dye is not [2-[N-(3-dimethylaminopropyl)-N-propylamino]-4-[2,3-dihydro-3-methyl-(benzo-1,3-thiazol-2-yl)-methylidene]-1-phenyl-quinolinium]+. In some embodiments, the conditions suitable for extension comprise $Mg^{++}$. In some embodiments, the conditions suitable for extension comprise $Mn^{++}$.

The present disclosure also provides a kit useful in such a polynucleotide extension method. Generally, the kit includes at least one container providing a mutant or improved DNA polymerase as described herein. In certain embodiments, the kit further includes one or more additional containers providing one or more additional reagents. For example, in specific variations, the one or more additional containers provide nucleoside triphosphates; a buffer suitable for polynucleotide extension; and/or one or more primer or probe polynucleotides, hybridizable, under polynucleotide extension conditions, to a predetermined polynucleotide template. The polynucleotide template can be from any type of biological sample.

Further provided are reaction mixtures comprising the polymerases described herein. The reaction mixtures can also contain a template nucleic acid (DNA and/or RNA), one or more primer or probe polynucleotides, nucleoside triphosphates (including, e.g., deoxyribonucleoside triphosphates, ribonucleoside triphosphates, labeled nucleoside triphosphates, unconventional nucleoside triphosphates), buffers, salts, labels (e.g., fluorophores). In some embodiments, the reaction mixtures comprise an iron chelator or a purple dye. In certain embodiments, the reaction mixtures comprise hemoglobin, or a degradation product of hemoglobin. For example, in certain embodiments, the degradation products of hemoglobin include heme breakdown products such as hemin, hematin, hematophoryn, and bilirubin.

In other embodiments, the reaction mixtures comprise heparin or a salt thereof. Optionally, the reaction mixture comprises an intercalating dye (including but not limited to those described above or elsewhere herein). In certain embodiments, the reaction mixture contains a template nucleic acid that is isolated from blood. In other embodiments, the template nucleic acid is RNA and the reaction mixture comprises heparin or a salt thereof.

In some embodiments, the reaction mixture comprises two or more polymerases. For example, in some embodiments, the reaction mixture comprises an improved DNA polymerase having increased strand displacement activity as described herein, and another polymerase having increase reverse transcription efficiency (e.g., increased activity extending an RNA-template). In one embodiment, the reaction mixture comprises a blend of an improved DNA polymerase having increased strand displacement activity as described herein, and a second thermostable DNA-dependent polymerase. The second thermostable DNA-dependent polymerase can be a reversibly modified polymerase as described above such that the enzyme is inactive at temperatures suitable for the reverse transcription step, but is activated under suitable conditions, for example, at elevated temperatures of about 90° C. to 100° C. for a period of time up to about 12 minutes. Suitable conditions for activation of a reversibly inactivated thermostable polymerase are provided, for example, in a Hot Start PCR reaction. Examples of suitable second thermostable DNA-dependent polymerases are described in U.S. Pat. Nos. 5,773,258 and 5,677,152 to Birch et al., supra.

Further embodiments are described herein.

Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., *Biochemistry*, 5th ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101(24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al. (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25):14310-14315, Bacher et al. (2001) "Selection and Characterization of *Escherichia coli* Variants Capable of Growth on an Otherwise Toxic Tryptophan Analogue," *J. Bacteriol.* 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51):40324-40328, and Budisa et al. (2001) "Proteins with {beta}-(thienopyrrolyl)alanines as alternative chromophores and pharmaceutically active amino acids," *Protein Sci.* 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "biological sample" encompasses a variety of sample types obtained from an organism and can be used in a diagnostic or monitoring assay. The term encompasses urine, urine sediment, blood, saliva, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, biological fluids, and tissue samples.

The term "mutant," in the context of DNA polymerases of the present invention, means a polypeptide, typically recombinant, that comprises one or more amino acid substitutions relative to a corresponding, functional DNA polymerase.

The term "unmodified form," in the context of a mutant polymerase, is a term used herein for purposes of defining a mutant DNA polymerase of the present invention: the term "unmodified form" refers to a functional DNA polymerase that has the amino acid sequence of the mutant polymerase except at one or more amino acid position(s) specified as characterizing the mutant polymerase. Thus, reference to a mutant DNA polymerase in terms of (a) its unmodified form and (b) one or more specified amino acid substitutions means that, with the exception of the specified amino acid substitution(s), the mutant polymerase otherwise has an amino acid sequence identical to the unmodified form in the specified motif. The "unmodified polymerase" (and therefore also the modified form having increased reverse transcriptase efficiency, mismatch tolerance, extension rate and/or tolerance of RT and polymerase inhibitors) may contain additional mutations to provide desired functionality, e.g., improved incorporation of dideoxyribonucleotides, ribonucleotides, ribonucleotide analogs, dye-labeled nucleotides, modulating 5'-nuclease activity, modulating 3'-nuclease (or proofreading) activity, or the like. Accordingly, in carrying out the present invention as described herein, the unmodified form of a DNA polymerase is predetermined. The unmodified form of a DNA polymerase can be, for example, a wild-type and/or a naturally occurring DNA polymerase, or a DNA polymerase that has already been intentionally modified. An unmodified form of the polymerase is preferably a thermostable DNA polymerase, such as DNA polymerases from various thermophilic bacteria, as well as functional variants thereof having substantial sequence identity to a wild-type or naturally occurring thermostable polymerase. Such variants can include, for example, chimeric DNA polymerases such as, for example, the chimeric DNA polymerases described in U.S. Pat. Nos. 6,228,628 and 7,148,049, which are incorporated by reference herein in their entirety. In certain embodiments, the unmodified form of a polymerase has reverse transcriptase (RT) activity.

The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps17, *Thermus* species Z05, *Thermus caldophilus, Bacillus caldotenax, Thermotoga neopolitana,* and Thermosipho *africanus.*

The term "thermoactive" refers to an enzyme that maintains catalytic properties at temperatures commonly used for reverse transcription or anneal/extension steps in RT-PCR and/or PCR reactions (i.e., 45-80° C.). Thermostable enzymes are those which are not irreversibly inactivated or denatured when subjected to elevated temperatures necessary for nucleic acid denaturation. Thermoactive enzymes may or may not be thermostable. Thermoactive DNA polymerases can be DNA or RNA dependent from thermophilic species or from mesophilic species including, but not limited to, *Escherichia coli*, Moloney murine leukemia viruses, and Avian myoblastosis virus.

As used herein, a "chimeric" protein refers to a protein whose amino acid sequence represents a fusion product of subsequences of the amino acid sequences from at least two distinct proteins. A chimeric protein typically is not produced by direct manipulation of amino acid sequences, but, rather, is expressed from a "chimeric" gene that encodes the chimeric amino acid sequence. In certain embodiments, for example, an unmodified form of a mutant DNA polymerase of the present invention is a chimeric protein that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

The term "aptamer" refers to a single-stranded DNA that recognizes and binds to DNA polymerase, and efficiently inhibits the polymerase activity as described in U.S. Pat. No. 5,693,502, hereby expressly incorporated by reference herein in its entirety. Use of aptamer and dUTP/UNG in RT-PCR is also discussed, for example, in Smith, E. S. et al, (Amplification of RNA: High-temperature Reverse Transcription and DNA Amplification with a Magnesium-activated Thermostable DNA Polymerase, in PCR Primer: A Laboratory Manual, 2nd Edition, Dieffenbach, C. W. and Dveksler, G. S., Ed., Cold Spring Harbor Laboratory Press, Cold Spring Harbor, New York, 211-219, (2003)).

In the context of mutant DNA polymerases, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. An amino acid "corresponding to position [X] of [specific sequence]" refers to an amino acid in a polypeptide of interest that aligns with the equivalent amino acid of a specified sequence. Generally, as described herein, the amino acid corresponding to a position of a polymerase can be determined using an alignment algorithm such as BLAST as described below. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase refers to equivalent positions, based on alignment, in other DNA polymerases and structural homologues and families. In some embodiments of the present invention, "correspondence" of amino acid positions are determined with respect to a region of the polymerase comprising one or more motifs of SEQ ID NO:1, 2, 3, 4, 5, 6, 7, 32, 33, 34, 35, 36, 37, or 39. When a polymerase polypeptide sequence differs from SEQ ID NOS:1, 2, 3, 4, 5, 6, 7, 32, 33, 34, 35, 36, 37, or 39 (e.g., by changes in amino acids or addition or deletion of amino acids), it may be that a particular mutation associated with improved activity as discussed herein will not be in the same position number as it is in SEQ ID NOS:1, 2, 3, 4, 5, 6, 7, 32, 33, 34, 35, 36, 37, or 39. This is illustrated, for example, in Table 1.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by restriction endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "primer" as used herein refers to a polynucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISA assays), biotin, or haptens and proteins for which antisera or monoclonal antibodies are available.

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-$PO_4$ analogs of ribonucleotides (see, e.g., U.S. Application Publication Nos. 2005/0037991 and 2005/0037398, which are both incorporated by reference). Other unconventional nucleotides include phosphorothioate dNTPs ([α-S]dNTPs), 5'-[α-borano]-dNTPs, [α]-methyl-phosphonate dNTPs, and ribonucleoside triphosphates (rNTPs).

Unconventional bases may be labeled with radioactive isotopes such as $^{32}P$, $^{33}P$, or $^{35}S$; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, MA), Applied Biosystems (Foster City, CA), or Invitrogen/Molecular Probes (Eugene, OR). Dyes of the cyanine family include Cy2, Cy3, Cy5, and Cy7 and are marketed by GE Healthcare UK Limited (Amersham Place, Little Chalfont, Buckinghamshire, England).

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region)), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Examples of an algorithm that is suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (see the internet at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, and an expectation (E) of 10, M=5, N=−4.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

The term "reverse transcription efficiency" refers to the fraction of RNA molecules that are reverse transcribed as cDNA in a given reverse transcription reaction. In certain embodiments, the mutant DNA polymerases of the invention have improved reverse transcription efficiencies relative to unmodified forms of these DNA polymerases. That is, these mutant DNA polymerases reverse transcribe a higher fraction of RNA templates than their unmodified forms under a particular set of reaction conditions. Without being limited by theory, the ability of a mutant DNA polymerase described herein to reverse transcribe a higher fraction of RNA templates can be due to an increased reverse transcription activity, for example, an increased nucleotide incorporation rate and/or increased processivity of the enzyme. Reverse transcription efficiency can be measured, for example, by measuring the crossing point (Cp) of a PCR reaction using a RNA template, and comparing the Cp value to a Cp value of a control reaction in which a DNA template of the same sequence (except U's are replaced with T's) is amplified, wherein the RNA and DNA amplifications use a common primer set and the same polymerase, e.g., as described in the examples. A test polymerase has improved RT efficiency when the test polymerase has a decreased Cp value compared to a control polymerase when RNA is used as a template, but has a substantially unchanged Cp value relative to the control polymerase when DNA is used as a template. In some embodiments a polymerase of the invention has an improved RT efficiency such that the Cp is at least one, two, three, four, five, six, seven, eight, nine, ten or more units less than the corresponding control polymerase on the RNA template.

The term "mismatch tolerance" refers to the ability of a polymerase to tolerate a mismatch-containing sequence when extending a nucleic acid (e.g., a primer or other oligonucleotide) in a template-dependent manner by attaching (e.g., covalently) one or more nucleotides to the nucleic acid. The term "3' mismatch tolerance" refers to the ability of a polymerase to tolerate a mismatch-containing (nearly complementary) sequence where the nucleic acid to be extended (e.g., a primer or other oligonucleotide) has a mismatch with its template at the 3' terminal nucleotide of the primer. Mismatches to the template may also be located at the 3' penultimate nucleotide of the primer, or at another position within the sequence of the primer.

The term "mismatch discrimination" refers to the ability of a polymerase to distinguish a fully complementary sequence from a mismatch-containing sequence when extending a nucleic acid (e.g., a primer or other oligonucle-otide) in a template-dependent manner by attaching (e.g., covalently) one or more nucleotides to the nucleic acid. The term "3'-mismatch discrimination" refers to the ability of a polymerase to distinguish a fully complementary sequence from a mismatch-containing (nearly complementary) sequence where the nucleic acid to be extended (e.g., a primer or other oligonucleotide) has a mismatch at the nucleic acid's 3' terminus compared to the template to which the nucleic acid hybridizes. The term "mismatch" refers to the existence of one or more base mispairings (or "non-complementary base oppositions") within a stretch of otherwise complementary duplex-forming (or potentially duplex-forming) sequences.

The term "Cp value" or "crossing point" value refers to a value that allows quantification of input target nucleic acids. The Cp value can be determined according to the second-derivative maximum method (Van Luu-The, et al., "Improved real-time RT-PCR method for high-throughput measurements using second derivative calculation and double correction," BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region (Van Luu-The, et al., BioTechniques, Vol. 38, No. 2, February 2005, pp. 287-293). The Cp value provided by the LightCycler instrument offered by Roche by calculation according to the second-derivative maximum method.

The term "PCR efficiency" refers to an indication of cycle to cycle amplification efficiency. PCR efficiency is calculated for each condition using the equation: % PCR efficiency=$(10^{(-slope)}-1)\times100$, wherein the slope was calculated by linear regression with the log copy number plotted on the y-axis and Cp plotted on the x-axis. PCR efficiency can be measured using a perfectly matched or mismatched primer template.

The term "nucleic acid extension rate" refers the rate at which a biocatalyst (e.g., an enzyme, such as a polymerase, ligase, or the like) extends a nucleic acid (e.g., a primer or other oligonucleotide) in a template-dependent or template-independent manner by attaching (e.g., covalently) one or more nucleotides to the nucleic acid. To illustrate, certain mutant DNA polymerases described herein have improved nucleic acid extension rates relative to unmodified forms of these DNA polymerases, such that they can extend primers at higher rates than these unmodified forms under a given set of reaction conditions.

The term "tolerance of RT and polymerase inhibitors" refers to the ability of a polymerase to maintain activity (polymerase or reverse transcription activity) in the presence of an amount of an inhibitor that would inhibit the polymerase activity or reverse transcription activity of a control polymerase. In some embodiments, the improved polymerase is capable of polymerase or reverse transcription activity in the presence of an amount of the inhibitor that would essentially eliminate the control polymerase activity.

The term "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light emitting moiety (e.g., a fluorescent dye, etc.). In certain embodiments, 5'-nuclease probes include regions of self-complementarity such that the probes are capable of forming hairpin structures under selected conditions. To further illustrate, in some embodiments a 5'-nuclease probe comprises at least two labeling moieties and emits radiation of increased intensity after one of the two labels is cleaved or otherwise separated from the oligonucleotide. In certain embodiments, a 5'-nuclease probe is labeled with two different fluorescent dyes, e.g., a 5' terminus reporter dye and the 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission of the reporter dye is no longer quenched. Exemplary 5'-nuclease probes are also described in, e.g., U.S. Pat. No. 5,210,015, entitled "Homogeneous assay system using the nuclease activity of a nucleic acid polymerase," issued May 11, 1993 to Gelfand et al., U.S. Pat. No. 5,994,056, entitled "Homogeneous methods for nucleic acid amplification and detection," issued Nov. 30, 1999 to Higuchi, and U.S. Pat. No. 6,171,785, entitled "Methods and devices for homogeneous nucleic acid amplification and detector," issued Jan. 9, 2001 to Higuchi, which are each incorporated by reference herein. In other embodiments, a 5' nuclease probe may be labeled with two or more different reporter dyes and a 3' terminus quencher dye or moiety.

The term "FRET" or "fluorescent resonance energy transfer" or "Foerster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™ (Integrated DNA Tech., Inc., Coralville, Iowa), and BlackBerry™ Quencher 650 (BBQ-650) (Berry & Assoc., Dexter, Mich.).

The term "strand displacement activity" refers to the ability of a polymerase to displace downstream DNA encountered during synthesis. The Royal Society of Chemistry defines the term "strand displacement" as "the rejection of the broken 3' single-strand DNA molecule that formed heteroduplex DNA with its complement in an intact duplex DNA. The Watson-Crick base pairing in the original duplex is restored. The rejected 3' single-strand DNA molecule reanneals with its original complement to reform two intact duplex molecules." In some embodiments, the term includes an isothermal amplification method termed Strand Displacement Amplification (SDA).

The term "elevated temperature" refers to a temperature above the melting temperature of double stranded DNA molecules. The melting temperature (Tm) is defined as the temperature at which half of the DNA strands are in the random coil or single-stranded (ssDNA) state. As is well known in the art, Tm depends on the length of the DNA molecule and its specific nucleotide sequence. Typical examples of elevated temperatures are encountered in PCR denaturing, annealing, and extension reactions, such as 60° C. or above, for example, from about 60° C. to about 95° C.

BRIEF DESCRIPTION OF THE DRAWINGS

FIG. 1 provides sequence identities among the following DNA Polymerase I enzymes: Thermus sp. Z05 DNA polymerase (Z05); Thermus aquaticus DNA polymerase (Taq); Thermus filiformis DNA polymerase (Tfi); Thermus flavus DNA polymerase (Tfl); Thermus sp. sps17 DNA polymerase (Sps17); Thermus thermophilus DNA polymerase (Tth); Thermus caldophilus DNA polymerase (Tca); Deinococcus radiodurans DNA polymerase (Dra); Thermotoga maritima DNA polymerase (Tma); Thermotoga neopolitana DNA polymerase (Tne); Thermosipho africanus DNA polymerase (Taf); Bacillus stearothermophilus DNA polymerase (Bst); and Bacillus caldotenax DNA polymerase (Bca). (A) sequence identities over the entire polymerase I enzyme (corresponding to amino acids 1-834 of Z05); and (B) sequence identities over the polymerase sub domain corresponding to amino acids 420-834 of Z05.

FIG. 2 provides sequence identities among various Thermus sp DNA Polymerase I enzymes: Thermus sp. Z05 DNA polymerase (Z05); Thermus aquaticus DNA polymerase (Taq); Thermus filiformis DNA polymerase (Tfi); Thermus flavus DNA polymerase (Tfl); Thermus sp. sps17 DNA polymerase (Sps17); Thermus thermophilus DNA polymerase (Tth); and Thermus caldophilus DNA polymerase (Tca). (A) sequence identities over the entire polymerase I enzyme (corresponding to amino acids 1-834 of Z05); and (B) sequence identities over the polymerase sub domain corresponding to amino acids 420-834 of Z05.

FIG. 4A shows the results of wells with bacterial colonies (clones) that expressed mutant polymerases having increased strand displacement activity compared to the control G46E C21 clone. Plate 6 shows the results for the G46E C21 clones (all wells of Plate 6 contained the original G46E C21 clone). Plate 1 shows increased strand displacement activity for following clones, which were subsequently sequenced: F24 (comprising the I686V and A693V mutations), L3 (comprising the T516I and V633I mutations), and P19 (comprising the Q415H, E420D, E636G, N752S, and V768M mutations).

FIG. 4B shows the result for plates 2-5. Plate 6 (above) served as the control for all these experiments. Plate 2 shows increased strand displacement activity for following clones with subsequent sequencing results for clone: M22 (comprising the R525G and F694S mutations), G9 (comprising the Q491H and T516S mutations), N19 (comprising the S515F and T666M mutations), and N7 (comprising the E402V, V555A and N582D mutations). Plate 3 shows increased strand displacement activity for following clones with subsequent sequencing results for clones: A24 (comprising the A737T and A759T mutations), F21 (comprising the L521Q and T546A mutations), G10 (comprising the N668S mutation), and 114 (comprising the A456T mutation). Plate 4 shows increased strand displacement activity for following clones with subsequent the sequencing results for clones: G23 (comprising the K507M, T571A and S652F mutations), and K12 (comprising the S515F and A832V mutations). Plate 5 shows increased strand displacement activity for following clones with subsequent sequencing results for clones C6 (comprising the D498E, L524V, R598G and M616I mutations), G20 (comprising the A444T, D498E, M660K and Y673N mutations), G23 (comprising the E493D, T511S, M648I and M749L mutations), and H21 (comprising the Q635K mutation).

DETAILED DESCRIPTION

Figure 3:
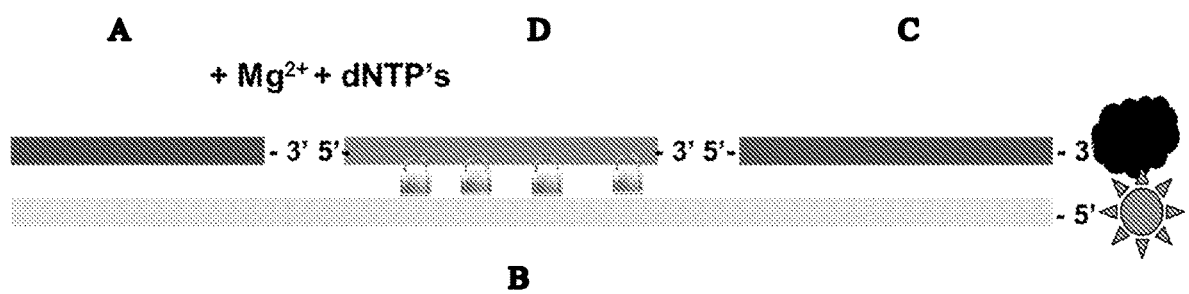
FIG. 3 shows the assay design described in the Examples. Four complimentary oligonucleotides Oligo A (green), Oligo B (light blue), Oligo C (dark blue) and Locked Nucleic Acid (LNA) Oligo D (red) were annealed to each other. Oligo A is complimentary to Oligo B and initiates polymerization reaction. Oligo B is the template and has a FAM—fluorescent reporter at the 5'-end. Oligo C is complimentary to Oligo B and has a BHQ quencher at the 3'-end. Locked Nucleic Acid Oligo D is complimentary to template Oligo B and serves as a high energy hurdle. When Polymerase, $Mg^{2+}$ and nucleotides are added to the annealed mixture the polymerization reaction extends Oligo A and the newly synthesized strand displaces the LNA Oligo D and Oligo C, thus releasing the quencher from fluorescent probe. A fluorescent signal is generated upon completion of the cycle.

The present disclosure provides improved DNA polymerases in which one or more amino acids in the polymerase domain have been mutated relative to a functional DNA polymerase. The DNA polymerases described herein are active enzymes having increased strand displacement activity relative to the unmodified form of the polymerase and/or increased mismatch tolerance, extension rate and tolerance of RT and polymerase inhibitors. In certain embodiments, the mutant DNA polymerases may be used at lower concentrations for superior or equivalent performance as the parent enzymes. In some embodiments, the mutant DNA polymerases have increased strand displacement activity while retaining substantially the same DNA-dependent polymerase activity relative to an unmodified or control polymerase. In some embodiments, the mutant DNA polymerases have substantially reduced exonuclease or endonuclease activity. In some embodiments the mutant DNA polymerases have decreased 5' to 3' exonuclease activity.

DNA polymerases having increased strand displacement activity are useful, for example, in Polymerase Chain Reaction (PCR) and isothermal amplification (such as strand displacement amplification (SDA)) at higher temperatures, and in techniques for DNA amplification such as loop-mediated amplification (LAMP), cross-priming amplification (CSA) and Polymerase Chain Displacement Reaction (PCDR). The DNA polymerases are therefore useful in a variety of applications involving polynucleotide extension, including, for example, applications in recombinant DNA studies and medical diagnosis of disease.

In some embodiments, the DNA polymerase further comprises the motif of SEQ ID NO:29 and/or SEQ ID NO:38.

This motif is present within the "fingers" domain (L alpha helix) of many Family A type DNA-dependent DNA polymerases, particularly thermostable DNA polymerases from thermophilic bacteria (Li et al., EMBO J. 17:7514-7525, 1998). For example, FIG. 1 shows an amino acid sequence alignment of a region from the "fingers" domain of DNA polymerases from several species of bacteria: *Bacillus caldotenax*, *Bacillus stearothermophilus*, *Deinococcus radiodurans*, Thermosipho *africanus*, *Thermotoga maritima*, *Thermotoga neopolitana*, *Thermus aquaticus*, *Thermus caldophilus*, *Thermus filiformus*, *Thermus flavus*, *Thermus sp. sps17*, *Thermus sp. Z05*, and *Thermus thermophilus*. As shown, the native sequence corresponding to the motif above is present in each of these polymerases, indicating a conserved function for this region of the polymerase. FIG. 2 provides sequence identities among these DNA polymerases.

In some embodiments, the polymerase having the improved activity and/or characteristics described herein is otherwise a wild-type or a naturally occurring DNA polymerase, such as, for example, a polymerase from any of the species of thermophilic bacteria listed above, or is substantially identical to such a wild-type or a naturally occurring DNA polymerase. For example, in some embodiments, the polymerase is at least 80%, 85%, 90%, or 95% identical to SEQ ID NO:1, 2, 3, 4, 5, 6, 7, 32, 33, 34, 35, 36, 37, 39, 40 or 42. In one variation, the unmodified form of the polymerase is from a species of the genus *Thermus*. In other embodiments of the invention, the unmodified polymerase is from a thermophilic species other than *Thermus*, e.g., *Thermotoga*. The full nucleic acid and amino acid sequence for numerous thermostable DNA polymerases are available. The sequences each of *Thermus aquaticus* (Taq) (SEQ ID NO:2), *Thermus thermophilus* (Tth) (SEQ ID NO:6), *Thermus* species Z05 (SEQ ID NO:1), *Thermus* species sps17 (SEQ ID NO:5), *Thermotoga maritima* (Tma) (SEQ ID NO:34), and Thermosipho *africanus* (Taf) (SEQ ID NO:33) polymerase have been published in PCT International Patent Publication No. WO 92/06200, which is incorporated herein by reference. The sequence for the DNA polymerase from *Thermus flavus* (SEQ ID NO:4) has been published in Akhmetzjanov and Vakhitov (*Nucleic Acids Research* 20:5839, 1992), which is incorporated herein by reference. The sequence of the thermostable DNA polymerase from *Thermus caldophilus* (SEQ ID NO:7) is found in EMBL/GenBank Accession No. U62584. The sequence of the thermostable DNA polymerase from *Thermus filiformis* can be recovered from ATCC Deposit No. 42380 using, e.g., the methods provided in U.S. Pat. No. 4,889,818, as well as the sequence information provided in Table 1. The sequence of the *Thermotoga neapolitana* DNA polymerase (SEQ ID NO:35) is from GeneSeq Patent Data Base Accession No. R98144 and PCT WO 97/09451, each incorporated herein by reference. The sequence of the thermostable DNA polymerase from *Bacillus caldotenax* (SEQ ID NO:37 is described in, e.g., Uemori et al. (*J Biochem* (Tokyo) 113(3): 401-410, 1993; see also, Swiss-Prot database Accession No. Q04957 and GenBank Accession Nos. D12982 and BAA02361), which are each incorporated by reference. Examples of unmodified forms of DNA polymerases that can be modified as described herein are also described in, e.g., U.S. Pat. No. 6,228,628, entitled "Mutant chimeric DNA polymerase" issued May 8, 2001 to Gelfand et al.; U.S. Pat. No. 6,346,379, entitled "Thermostable DNA polymerases incorporating nucleoside triphosphates labeled with fluorescein family dyes" issued Feb. 12, 2002 to Gelfand et al.; U.S. Pat. No. 7,030,220, entitled "Thermostable enzyme promoting the fidelity of thermostable DNA polymerases—for improvement of nucleic acid synthesis and amplification in vitro" issued Apr. 18, 2006 to Ankenbauer et al.; U.S. Pat. No. 6,881,559 entitled "Mutant B-type DNA polymerases exhibiting improved performance in PCR" issued Apr. 19, 2005 to Sobek et al.; U.S. Pat. No. 6,794,177 entitled "Modified DNA-polymerase from *Carboxydothermus hydrogenoformans* and its use for coupled reverse transcription and polymerase chain reaction" issued Sep. 21, 2004 to Markau et al.; U.S. Pat. No. 6,468,775, entitled "Thermostable DNA polymerase from *Carboxydothermus hydrogenoformans*" issued Oct. 22, 2002 to Ankenbauer et al.; and U.S. Pat. No. 7,148,049 entitled "Thermostable or thermoactive DNA polymerase molecules with attenuated 3'-5' exonuclease activity" issued Dec. 12, 2006 to Schoenbrunner et al.; U.S. Pat. No. 7,179,590 entitled "High temperature reverse transcription using mutant DNA polymerases" issued Feb. 20, 2007 to Smith et al.; U.S. Pat. No. 7,410,782 entitled "Thermostable enzyme promoting the fidelity of thermostable DNA polymerases—for improvement of nucleic acid synthesis and amplification in vitro" issued Aug. 12, 2008 to Ankenbauer et al.; U.S. Pat. No. 7,378,262 entitled "Reversibly modified thermostable enzymes for DNA synthesis and amplification in vitro" issued May 27, 2008 to Sobek et al., which are each incorporated by reference. Representative full length polymerase sequences are also provided in the sequence listing.

Also amenable to the mutations described herein are functional DNA polymerases that have been previously modified (e.g., by amino acid substitution, addition, or deletion). In some embodiments, such functional modified polymerases comprise the amino sequence of SEQ ID NO: 40 or SEQ ID NO:42, or have substantial sequence identity or similarity to SEQ ID NO: 40 or SEQ ID NO:42, for example, at least 80%, 85%, 90%, 91%, 92%, 93%, 94%, 95%, 96%, 97%, 98% or 99% sequence identity to SEQ ID NO: 40 or SEQ ID NO:42. In some embodiments, suitable unmodified DNA polymerases also include functional variants of wild-type or naturally occurring polymerases. Such variants typically will have substantial sequence identity or similarity to the wild-type or naturally occurring polymerase, typically at least 80% sequence identity and more typically at least 90%, 91%, 92%, 93%, 94%, 95%, 96%, 97%, 98% or 99% sequence identity.

In some embodiments, the polymerases described herein also comprise a nuclease domain (e.g., corresponding to positions 1 to 291 of Z05 (SEQ ID NO:1)).

In some embodiments, a polymerase described herein is a chimeric polymerase, i.e., comprising polypeptide regions from two or more enzymes. Examples of such chimeric DNA polymerases are described in, e.g., U.S. Pat. No. 6,228,628, which is incorporated by reference herein in its entirety. Particularly suitable are chimeric CS-family DNA polymerases, which include the CS5 (SEQ ID NO:27) and CS6 (SEQ ID NO:28) polymerases and variants thereof having substantial amino acid sequence identity or similarity to SEQ ID NO:27 or SEQ ID NO:28 (typically at least 80% amino acid sequence identity and more typically at least 90%, 91%, 92%, 93%, 94%, 95%, 96%, 97%, 98% or 99% amino acid sequence identity). The CS5 and CS6 DNA polymerases are chimeric enzymes derived from *Thermus* sp. Z05 and *Thermotoga maritima* (Tma) DNA polymerases. They comprise the N-terminal 5'-nuclease domain of the *Thermus* enzyme and the C-terminal 3'-5' exonuclease and the polymerase domains of the Tma enzyme. These enzymes have efficient reverse transcriptase activity, can extend nucleotide analog-containing primers, and can incorporate alpha-phosphorothioate dNTPs, dUTP, dITP, and also fluorescein- and cyanine-dye family labeled dNTPs. The CS5 and CS6 polymerases are also efficient $Mg^{2+}$-activated PCR enzymes. The CS5 and CS6 chimeric polymerases are further described in, e.g., U.S. Pat. No. 7,148,049, which is incorporated by reference herein in its entirety.

In some embodiments, the amino acid substitutions are single amino acid substitutions. The DNA polymerases provided herein can comprise one or more amino acid substitutions in the active site relative to the unmodified polymerase.

In some embodiments, the polymerases described herein further comprise the amino acid motif of SEQ ID NO:38 (corresponding to the D580X mutation of Z05 (SEQ ID NO:1)) as follows:
Thr-Gly-Arg-Leu-Ser-Ser-$X_7$-$X_8$-Pro-Asn-Leu-Gln-Asn (also referred to herein in the one-letter code as T-G-R-L-S-S-$X_7$-$X_8$-P-N-L-Q-N) (SEQ ID NO:38); wherein
$X_7$ is Ser (S) or Thr (T); and
$X_8$ is any amino acid other than Asp (D) or Glu (E)
The mutation characterized by SEQ ID NO:38 is discussed in more detail in, e.g., US Patent Publication No. 2009/0148891. Such functional variant polymerases typically will have substantial sequence identity or similarity to the wild-type or naturally occurring polymerase (e.g., SEQ ID NO:1, 2, 3, 4, 5, 6, 7, 32, 33, 34, 35, 36, 37, 39, 40 and 42), typically at least 80% amino acid sequence identity and more typically at least 90%, 91%, 92%, 93%, 94%, 95%, 96%, 97%, 98% or 99% amino acid sequence identity.

In some embodiments, the polymerases described herein further comprise the amino acid motif of SEQ ID NO:29 (corresponding to the I709X mutation of Z05 (SEQ ID NO:1)) as follows:
$X_1$-$X_2$-$X_3$-$X_4$-$X_5$-$X_6$-$X_7$-$X_8$-$X_9$-$X_{10}$-$X_{11}$-$X_{12}$-$X_{13}$-Gly-Tyr-Val-$X_{14}$-Thr-Leu (also referred to herein in the one-letter code as $X_1$-$X_2$-$X_3$—$X_4$-$X_5$-$X_6$-$X_7$-$X_8$-$X_9$-$X_{10}$-$X_{11}$-$X_{12}$-$X_{13}$-G-Y-V-$X_{14}$-T-L) (SEQ ID NO:29); wherein
$X_1$ is Ala (A), Asp (D), Ser (S), Glu (E), Arg (R) or Gln (Q);
$X_2$ is Trp (W) or Tyr (Y);
$X_3$ is any amino acid other than Ile (I), Leu (L) or Met (M);
$X_4$ is Glu (E), Ala (A), Gln (Q), Lys (K), Asn (N) or Asp (D);
$X_5$ is Lys (K), Gly (G), Arg (R), Gln (Q), His (H) or Asn (N);
$X_6$ is Thr (T), Val (V), Met (M) or Ile (I);
$X_7$ is Leu (L), Val (V) or Lys (K);
$X_8$ is Glu (E), Ser (S), Ala (A), Asp (D) or Gln (Q);
$X_9$ is Glu (E) or Phe (F);
$X_{10}$ is Gly (G) or Ala (A);
$X_{11}$ is Arg (R) or Lys (K);
$X_{12}$ is Lys (K), Arg (R), Glu (E), Thr (T) or Gln (Q);
$X_{13}$ is Arg (R), Lys (K) or His (H); and
$X_{14}$ is Glu (E), Arg (R) or Thr (T).
In some embodiments, such functional variant polymerases typically will have substantial sequence identity or similarity to the wild-type or naturally occurring polymerase (e.g., SEQ ID NO:1, 2, 3, 4, 5, 6, 7, 32, 33, 34, 35, 36, 37, 39, 40 or 42), typically at least 80% amino acid sequence identity and more typically at least 90%, 91%, 92%, 93%, 94%, 95%, 96%, 97%, 98% or 99% amino acid sequence identity.

In some embodiments, the DNA polymerase comprises an amino acid substitution corresponding to SEQ ID NO:38 and SEQ ID NO:29. In some embodiments, amino acid substitutions include Leucine (L), Glycine (G), Threonine (T), Glutamine (Q), Alanine (A), Serine (S), Asparagine (N), Arginine (R), and Lysine (K) at position $X_8$ of SEQ ID NO:38. In certain embodiments, the amino acid substitution includes Glycine (G) at position $X_8$ of SEQ ID NO:38. In some embodiments, amino acid substitutions include Lysine (K), Arginine (R), Serine (S), Glycine (G) or Alanine (A) at position $X_3$ of SEQ ID NO:29. In certain embodiments, the amino acid substitution includes Lysine (K) at position $X_3$ of SEQ ID NO:29.

Other suitable amino acid substitution(s) at one or more of the identified sites can be determined using, e.g., known methods of site-directed mutagenesis and determination of polynucleotide extension performance in assays described further herein or otherwise known to persons of skill in the art, e.g., amino acid substitutions described in U.S. Pat. Application Publication Nos. 2009/0148891 and 2009/0280539, which are incorporated by reference herein in its entirety.

Because the precise length of DNA polymerases vary, the precise amino acid positions corresponding to $X_8$ (SEQ ID NO:38) and $X_3$ (SEQ ID NO:29) can vary depending on the particular mutant polymerase used. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention. The positions corresponding to $X_8$ and $X_3$ are shown in Table 1 for representative chimeric thermostable DNA polymerases and thermostable DNA polymerases from exemplary thermophilic species.

TABLE 1

AMINO ACID POSITIONS CORRESPONDING TO MOTIF POSITIONS $X_8$ (OF SEQ ID NO: 38) AND $X_3$ (OF SEQ ID NO: 29) IN EXEMPLARY POLYMERASES.

| Organism or Chimeric Sequence Consensus (SEQ ID NO:) | Amino Acid Position | |
|---|---|---|
| | $X_8$ (of SEQ ID NO: 38) | $X_3$ (of SEQ ID NO: 29) |
| T. thermophilus (6) | 580 | 709 |
| T. caldophilus (7) | 580 | 709 |
| T. sp. Z05 (1) | 580 | 709 |
| T. aquaticus (2) | 578 | 707 |
| T. flavus (4) | 577 | 706 |
| T. filiformis (3) | 576 | 705 |
| T. sp. sps17 (5) | 576 | 705 |
| T. maritima (34) | 640 | 770 |
| T. neapolitana (35) | 640 | 770 |
| T. africanus (33) | 639 | 769 |
| B. caldotenax (37) | 621 | 751 |
| B. stearothermophilus (36) | 620 | 750 |
| CS5 (27) | 640 | 770 |
| CS6 (28) | 640 | 770 |

In some embodiments, the DNA polymerase of the present invention is derived from Thermus sp. Z05 DNA polymerase (SEQ ID NO: 1) or a variant thereof (e.g., carrying the D580G mutation or the like). As referred to above, in Thermus sp. Z05 DNA polymerase, position $X_8$ corresponds to Aspartate (D) at position 580, and position $X_3$ corresponds to Isoleucine (I) at position 709. Thus, in certain variations of the invention, the mutant polymerase further comprises at least one amino acid substitution, relative to a Thermus sp. Z05 DNA polymerase (or a DNA polymerase that is substantially identical, e.g., at least about 60%, 65%, 70%, 75%, 80%, 85%, 90%, or 95% identical to SEQ ID NO: 1), at D580 and/or 1709. In certain embodiments, amino acid residues at position 580 of SEQ ID NO:1 can be selected from Leucine (L), Glycine (G), Threonine (T), Glutamine (Q), Alanine (A), Serine (S), Asparagine (N), Arginine (R), and Lysine (K). Thus, in some embodiments, the amino acid residue at position 580 of SEQ ID NO:1 is Glycine (G). Further, in certain embodiments, the amino acid at position 709 of SEQ ID NO:1 is not I. In some embodiments, the amino acid at position 709 of SEQ ID NO:1 is selected from G, A, V, R, F, W, P, S, T, C, Y, N, Q, D, E, K, L, M, or H. In some embodiments, the amino acid at position 709 of SEQ ID NO:1 is K, R, S, G or A. In some embodiments, the amino acid at position 709 of SEQ ID NO:1 is K.

Exemplary Thermus sp. Z05 DNA polymerase mutants include those comprising the amino acid substitution(s) I709K (or I709R, I709S, I709G, I709A), and/or D580G.

The inventors have shown that substitutions at the amino acid corresponding to position 709 of SEQ ID NO:1 described above can result in DNA polymerases having improved (i.e., increased) reverse transcription efficiency, increased RT-PCR activity (e.g., more efficient amplification of an RNA template without compromising PCR efficiency on a DNA template), increased RT-PCR efficiency in the presence of $Mg^{2+}$, increased reverse transcriptase activity in the presence of inhibitors (e.g., breakdown products of hemoglobin such as hemin, and/or heparin), increased extension rate and improved 3'-mismatch tolerance compared to a control polymerase. See U.S. Patent Application No. 61/474,160, filed Apr. 11, 2011, the contents of which are incorporated by reference herein in its entirety. Thus, it is expected that the improved polymerases that comprise substitutions at the amino acid corresponding to position 709 of SEQ ID NO:1 described herein will also have the improved properties described above.

In addition to the mutations and substitutions described herein, the DNA polymerases of the present invention can also include other, non-substitutional modification(s). Such modifications can include, for example, covalent modifications known in the art to confer an additional advantage in applications comprising polynucleotide extension. For example, one such modification is a thermally reversible covalent modification that inactivates the enzyme, but which is reversed to activate the enzyme upon incubation at an elevated temperature, such as a temperature typically used for polynucleotide extension. Exemplary reagents for such thermally reversible modifications are described in U.S. Pat. Nos. 5,773,258 and 5,677,152 to Birch et al., which are expressly incorporated by reference herein in their entirety.

The DNA polymerases of the present invention can be constructed by mutating the DNA sequences that encode the corresponding unmodified polymerase (e.g., a wild-type polymerase or a corresponding variant from which the polymerase of the invention is derived), such as by using techniques commonly referred to as site-directed mutagenesis. Nucleic acid molecules encoding the unmodified form of the polymerase can be mutated by a variety of polymerase chain reaction (PCR) techniques well-known to one of ordinary skill in the art. (See, e.g., PCR Strategies (M. A. Innis, D. H. Gelfand, and J. J. Sninsky eds., 1995, Academic Press, San Diego, CA) at Chapter 14; PCR Protocols: A Guide to Methods and Applications (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the polymerase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, NJ) to confirm that no other alterations in the sequence have occurred (by band shift comparison to the unmutagenized control). Alternatively, the entire DNA region can be sequenced to confirm that no additional mutational events have occurred outside of the targeted region.

DNA polymerases with more than one amino acid substituted can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified polymerase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids encoding any of the DNA polymerases of the present invention. Using a nucleic acid of the present invention, encoding a DNA polymerase, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the DNA polymerase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666, 848). The transcriptional and translational regulatory nucleic acid regions will generally be appropriate to the host cell used to express the polymerase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying a thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the polymerase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, NY, 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a DNA polymerase is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, viral infection, and the like.

In some embodiments, prokaryotes are typically used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.,* 204:63, 1991. Plasmids typically used for transformation of *E. coli* include pBR322, pUCI8, pUCI9, pUCII8, pUC119, and Bluescript M13, all of which are described in sections 1.12-1.20 of Sambrook et al., supra. However, many other suitable vectors are available as well.

The DNA polymerases of the present invention are typically produced by culturing a host cell transformed with an expression vector containing a nucleic acid encoding the DNA polymerase, under the appropriate conditions to induce or cause expression of the DNA polymerase. Methods of culturing transformed host cells under conditions suitable for protein expression are well-known in the art (see, e.g., Sambrook et al., supra). Suitable host cells for production of the polymerases from lambda pL promotor-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the polymerase can be harvested and isolated. Methods for purifying the thermostable DNA polymerase are described in, for example, Lawyer et al., supra. Once purified, the ability of the DNA polymerases to have increased strand displacement activity, improved RT efficiency, increased mis-match tolerance, extension rate and/or tolerance of RT and polymerase inhibitors can be tested (e.g., as described in the examples).

The improved DNA polymerases of the present invention may be used for any purpose in which such enzyme activity is necessary or desired. Accordingly, in another aspect of the invention, methods of polynucleotide extension (e.g., PCR) using the polymerases are provided. Conditions suitable for polynucleotide extension are known in the art. (See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the DNA polymerase and nucleoside triphosphates in a suitable environment to permit the addition of one or more nucleotides to the 3' end of the primer, thereby producing an extended primer complementary to the target nucleic acid. The primer can include, e.g., one or more nucleotide analog(s). In addition, the nucleoside triphosphates can be conventional nucleotides, unconventional nucleotides (e.g., ribonucleotides or labeled nucleotides), or a mixture thereof. In some variations, the polynucleotide extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; *PCR Applications: Protocols for Functional Genomics* (Innis et al. eds., Academic Press 1999). In other, non-mutually exclusive embodiments, the polynucleotide extension reaction comprises reverse transcription of an RNA template (e.g., RT-PCR). In some embodiments, the improved polymerases find use in 454 sequencing (Margulies, M et al. 2005, Nature, 437, 376-380).

Optionally, the primer extension reaction comprises an actual or potential inhibitor of a reference or unmodified polymerase. The inhibitor can inhibit, for example, the nucleic acid extension rate and/or the reverse transcription efficiency of a reference or unmodified (control) polymerase. In some embodiments, the inhibitor is hemoglobin, or a degradation product thereof. For example, in some embodiments, the hemoglobin degradation product is a heme breakdown product, such as hemin, hematoporphyrin, or bilirubin. In some embodiments, the inhibitor is an iron-chelator or a purple pigment. In other embodiments, the inhibitor is heparin. In certain embodiments, the inhibitor is an intercalating dye. In certain embodiments, the inhibitor is melanin, which has been described as a polymerase inhibitor. See, e.g, Ekhardt, et al., *Biochem Biophys Res Commun.* 271(3):726-30 (2000).

The DNA polymerases of the present invention can be used to extend templates in the presence of polynucleotide templates isolated from samples comprising polymerase inhibitors, e.g., such as blood. For example, the DNA polymerases of the present invention can be used to extend templates in the presence of hemoglobin, a major component of blood, or in the presence of a hemoglobin degradation product. Hemoglobin can be degraded to various heme breakdown products, such as hemin, hematin, hematoporphyrin, and bilirubin. Thus, in certain embodiments, the DNA polymerases of the present invention can be used to extend templates in the presence of hemoglobin degradation products, including but not limited to, hemin, hematin, hematoporphyrin, and bilirubin. In certain embodiments, the hemoglobin degradation product is hemin. In some embodiments, the DNA polymerases of the present invention can be used to extend templates in the presence of about 0.5 to 20.0 µM, about 0.5 to 10.0 µM, about 0.5 to 5.0 µM, about 1.0 to 10.0 µM, about 1.0 to 5.0 µM, about 2.0 to 5.0 µM, or about 2.0 to 3.0 µM hemin. In other embodiments, the DNA polymerases of the present invention can be used to extend templates in the presence of at least about 0.5, 1.0, 1.5, 2.0, 2.5, 3.0, 4.0, 5.0, 10.0, 20.0, or greater than 20 µM hemin. The breakdown products of hemoglobin include iron-chelators and purple pigments. Thus, in some embodiments, the DNA polymerases of the present invention can be used to extend templates in the presence of iron-chelators and/or purple pigments. In other embodiments, the DNA polymerases of the present invention can be used to extend templates in the presence of amounts of hemoglobin degradation products that would inhibit extension of the same template by a reference or control DNA polymerase.

The DNA polymerases of the present invention can be used to extend templates in the presence of heparin. Heparin is commonly present as an anticoagulant in samples isolated from blood. In some embodiments, the DNA polymerases of the present invention can be used to extend templates in the presence of about 1.0 to 400 ng/µl, 1.0 to 300 ng/µl, 1.0 to 200 ng/µl, 5.0 to 400 ng/µl, 5.0 to 300 ng/µl, 5.0 to 200 ng/µl, 10.0 to 400 ng/µl, 10.0 to 300 ng/µl, or 10.0 to 200 ng/µl heparin. In some embodiments, the DNA polymerases of the present invention can be used to extend templates in the presence of at least about 1, 2, 3, 4, 5, 6, 7, 8, 9, 10, 11, 12, 13, 14, 15, 20, 30, 40, 50, 100, 150, 200, 250, 300, 350, 400 ng/µl, or greater than 400 ng/µl of heparin. In other embodiments, the DNA polymerases of the present invention can be used to extend templates in the presence of amounts of heparin that would inhibit extension of the same template by a reference or control DNA polymerase.

In some embodiments, an improved polymerase described herein is used in a strand displacement reaction. In some embodiments, the strand displacement reaction is carried out in a mixture containing the DNA template, one or more primer(s), and a thermostable DNA polymerase described herein. The reaction mixture typically contains all four standard deoxyribonucleoside triphosphates (dNTPs) and a buffer containing a divalent cation and a monovalent cation. Exemplary cations include, e.g., $Mg^{2+}$, although other cations, such as $Mn^{2+}$ or $Co^{2+}$ can activate DNA polymerases. In other embodiments, the strand displacement reaction is carried out with a thermo-active DNA polymerase of the invention. In particular embodiments, the improved polymerases described herein allow for more efficient strand displacement reactions at elevated temperatures while at the same time having decreased exonuclease and/or endonuclease activity.

In some embodiments, the improved polymerase has increased strand displacerent activity compared to a control polymerase. It was not previously appreciated that amino acid substitutions at the corresponding positions of SEQ ID NO:1 or SEQ ID NO:40 described herein could result in increased strand displacement activity.

In some embodiments, the improved polymerase has increased reverse transcription efficiency using an RNA template without a substantial decrease in polymerase activity using a DNA template. Thus, in some embodiments, the improved DNA polymerase has increased RT efficiency without a substantial decrease in DNA-dependent polymerase activity when compared to a control polymerase. In some embodiments, the improved DNA polymerase described herein has DNA-dependent polymerase activity that is substantially the same as a control polyermerase. Thus, in some embodiments, the improved DNA polymerase described herein has DNA-dependent polymerase activity that is at least about 90% of the activity of a control polymerase, for example, at least about 90%, 91%, 92%, 93%, 94%, 95%, or more of the activity of a control polymerase. The DNA-dependent polymerase activity can be measured, for example, by amplifying a DNA template and determining Cp values as described herein. Thus, in some embodiments, the DNA polymerase has improved RT efficiency measured as a decreased Cp value compared to a control polymerase when RNA is used as a template, but has a substantially unchanged Cp value relative to the control polymerase when DNA is used as a template. For example, when amplifying a DNA template, the improved DNA polymerase can have a Cp value that differs by less than 1.0, less than 0.5, less than 0.4, less than 0.3, less than 0.2, or less than 0.1 compared to a control polymerase. In some embodiments, the DNA-dependent polymerase activity is determined as described in the Examples.

In some embodiments, an improved polymerase of the invention increases reverse transcription efficiency by reducing the reaction time required for extending an RNA template. For example, an improved polymerase described herein can significantly shorten the reaction time required to transcribe RNA to cDNA as compared to a control polymerase, thereby increasing the reverse transcriptase efficiency. Without being limited by theory, the improved polymerase can increase RT efficiency by, for example, increasing the activity of the enzyme on an RNA template, such as increasing the rate of nucleotide incorporation and/or increasing the processivity of the polymerase, thereby effectively shortening the extension time of an RNA template or population of RNA templates. Reaction times for the initial RT step are typically on the order of 30 minutes or longer at 65 degrees C. when using an unmodified or control polymerase. Thus, in some embodiments, the improved polymerase can transcribe an RNA template into cDNA in less than about 30 minutes, less than about 20 minutes, less than about 10 minutes, less than about 8 minutes, less than about 5 minutes, less than about 4 minutes, less than about 3 minutes, or less than about 2 minutes at 65 degrees C. In some embodiments, the improved polymerase can transcribe an RNA template derived from Hepatitis C Virus (HCV) transcript JP2-5, containing the first 800 bases of HCV genotype Ib 5'NTR, into cDNA in less time or faster than a control polymerase. For example, the improved polymerase can transcribe 240 bases of the HCV JP2-5 RNA template into full-length cDNA in about 15 seconds less, 30 seconds less, one minute less, two minutes less, 3 minutes less, 4 minutes less, 5 minutes less, or about 10 minutes less than a control polymerase under identical reaction conditions. In some embodiments, the improved polymerase can transcribe 240 bases of the HCV JP2-5 RNA template into full-length cDNA faster than a control polymerase, for example, about 5 seconds, 10 seconds, 15 seconds, 30 seconds, 45 seconds, or 60 seconds or more faster than a control polymerase under identical reaction conditions. In some embodiments, the reaction conditions are those described in the Examples. In some embodiments, an improved polymerase described herein is contacted with an RNA template at 65 degrees C. for about 2 minutes in the reaction mixture described above. The extension step can be followed by PCR amplification of the extended template, as described in the examples.

The most efficient RT activity in thermostable DNA polymerases has been achieved using $Mn^{2+}$ as the divalent metal ion activator. However, it is well known that when $Mn^{2+}$ is present in reactions the fidelity of DNA polymerases is lower. Unless one is trying to generate mutations, it is generally favored to maintain a higher fidelity. Fortunately, most conventional sequencing, PCR and RT-PCR applications do not require high fidelity conditions because the detection systems generally are looking at a population of products. With the advent of next generation sequencing, digital PCR, etc., the fidelity of the product is more important and methods that allow for higher fidelity DNA synthesis are critical. Achieving efficient RT activity using $Mg^{2+}$ as the divalent metal ion activator is an excellent way to substantially increase the fidelity of the DNA polymerase and allow for more reliable copying of the nucleic acid target. Accordingly, in some embodiments, the improved polymerase of the invention allows for efficient extension and/or amplification of RNA templates using $Mg^{2+}$ as the divalent metal ion activator, as described in the examples.

Because the polymerases described herein can also have increased mismatch tolerance, the polymerases find use in methods where variation of the target template is likely and yet the template is nevertheless desired to be amplified regardless of the variation at the target template. An example of such templates can include, for example, viral, bacterial, or other pathogen sequences. In many embodiments, it is desirable to determine simply whether an individual (human or non-human animal) has a viral or other infection, regardless of the precise viral variant that has infected the individual. As an example, one can use a primer pair to amplify HCV using a polymerase of the invention and detect the presence of the HCV even if the particular virus infecting the individual has a mutation resulting in a mismatch at the primer hybridization site.

Target nucleic acids can come from a biological or synthetic source. The target can be, for example, DNA or RNA. Generally, where amplicons are generated, the amplicons will be composed of DNA, though ribonucleotides or synthetic nucleotides can also be incorporated into the amplicon. Where one wishes to detect an RNA, the amplification process will typically involve the use of reverse transcription, including for example, reverse transcription PCR (RT-PCR).

Specific target sequences can include, e.g., viral nucleic acids (e.g., human immunodeficiency virus (HIV), hepatitis virus B (HBV), (cytomegalovirus (CMV), parvo B19 virus, Epstein-Barr virus, hepatitis virus C (HCV), human papilloma virus (HPV), Japanese encephalitis virus (JEV), West Nile virus (WNV), St. Louis encephalitis virus (SLEV), Murray Valley encephalitis virus, and Kunjin virus), bacterial nucleic acids (e.g., *S. aureus, Neisseria meningitidis, Plasmodium falciparum, Chlamydia muridarum, Chlamydia trachomatis*), mycobacteria, fungal nucleic acids, or nucleic acids from animals or plants. In some embodiments, the target nucleic acids are animal (e.g., human) nucleic acids or are derived from an animal (e.g., human) sample (i.e., viral or other pathogenic organism nucleic acids may be present in a sample from an animal biopsy, blood sample, urine sample, fecal sample, saliva, etc.). In some embodiments, the target nucleic acids are, for example, human genetic regions that may include variants associated with disease (e.g., cancer, diabetes, etc.). Because in some embodiments the polymerases of the invention have mismatch tolerance, such enzymes are particularly useful, for example, where a diversity of related sequences could be in a target sequence. As an example, the invention can be used to detect viral pathogens, where the viral pathogens have sufficient variation in their genomes to make it difficult or impossible to design a single or small set of primers that will amplify most or all possible viral genomes or in cancer or other disease genetic markers where variation in sequence is known or likely to occur.

Other methods for detecting extension products or amplification products using the improved polymerases described herein include the use of fluorescent double-stranded nucleotide binding dyes or fluorescent double-stranded nucleotide intercalating dyes. Examples of fluorescent double-stranded DNA binding dyes include SYBR-green (Molecular Probes). The double stranded DNA binding dyes can be used in conjunction with melting curve analysis to measure primer extension products and/or amplification products. The melting curve analysis can be performed on a real-time PCR instrument, such as the ABI 5700/7000 (96 well format) or ABI 7900 (384 well format) instrument with onboard software (SDS 2.1). Alternatively, the melting curve analysis can be performed as an end point analysis. Exemplary methods of melting point analysis are described in U.S. Patent Publication No. 2006/0172324, the contents of which are expressly incorporated by reference herein in its entirety.

In another aspect of the present invention, kits are provided for use in primer extension methods described herein. In some embodiments, the kit is compartmentalized for ease of use and contains at least one container providing an improved DNA polymerase in accordance with the present invention. One or more additional containers providing additional reagent(s) can also be included. In some embodiments, the kit can also include a blood collection tube, container, or unit that comprises heparin or a salt thereof, or releases heparin into solution. The blood collection unit can be a heparinized tube. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. For example, in certain embodiments, the kit further includes a container providing a 5' sense primer hybridizable, under primer extension conditions, to a predetermined polynucleotide template, or a primer pair comprising the 5' sense primer and a corresponding 3' antisense primer. In other, non-mutually exclusive variations, the kit includes one or more containers providing nucleoside triphosphates (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

In another aspect of the present invention, reaction mixtures are provided comprising the polymerases with increased reverse transcriptase efficiency, mismatch tolerance, extension rate and/or tolerance of RT and polymerase inhibitors as described herein. The reaction mixtures can further comprise reagents for use in, e.g., nucleic acid amplification procedures (e.g., PCR, RT-PCR), DNA sequencing procedures, or DNA labeling procedures. For example, in certain embodiments, the reaction mixtures comprise a buffer suitable for a primer extension reaction. The reaction mixtures can also contain a template nucleic acid (DNA and/or RNA), one or more primer or probe polynucleotides, nucleoside triphosphates (including, e.g., deoxyribonucleotides, ribonucleotides, labeled nucleotides, unconventional nucleotides), salts (e.g., $Mn^{2+}$, $Mg^{2+}$), labels (e.g., fluorophores). In some embodiments, the reaction mixtures contain a 5'-sense primer hybridizable, under primer extension conditions, to a predetermined polynucleotide template, or a primer pair comprising the 5'-sense primer and a corresponding 3' antisense primer. In some embodiments, the reaction mixtures contain alpha-phosphorothioate dNTPs, dUTP, dITP, and/or labeled dNTPs such as, e.g., fluorescein- or cyanin-dye family dNTPs. In some embodiments, the reaction mixtures comprise an iron chelator or a purple dye. In certain embodiments, the reaction mixtures comprise hemoglobin, or a degradation product of hemoglobin. For example, in certain embodiments, the degradation products of hemoglobin include heme breakdown products such as hemin, hematin, hematophoryn, and bilirubin. In other embodiments, the reaction mixtures comprise heparin or a salt thereof. In certain embodiments, the reaction mixture contains a template nucleic acid that is isolated from blood. In other embodiments, the template nucleic acid is RNA and the reaction mixture comprises heparin or a salt thereof.

In some embodiments, the reaction mixture comprises two or more polymerases. For example, in some embodiments, the reaction mixture comprises a first DNA polymerase having increased reverse transcriptase efficiency compared to a control polymerase, and a second DNA polymerase having DNA-dependent polymerase activity. The second DNA polymerase can be a wild-type or unmodified polymerase, or can be an improved polymerase having increased DNA-dependent polymerase activity. Such reaction mixtures are useful for amplification of RNA templates (e.g., RT-PCR) by providing both a polymerase having increased reverse transcriptase activity and a polymerase having DNA-dependent polymerase activity.

EXAMPLES

The following examples are offered to illustrate, but not to limit the claimed invention.

Example 1: Library Generation

In brief, the steps in this screening process included library generation, expression and partial purification of the mutant enzymes, screening of the enzymes for the desired properties, DNA sequencing, clonal purification, and further characterization of selected candidate mutants. Each of these steps is described further below.

Clonal Library generation: A nucleic acid encoding the G46E mutation of C21 DNA polymerase was subjected to error-prone (mutagenic) PCR using the GeneMorph II™ random mutagenesis kit for error-prone PCR (Agilent Technologies). The PCR fragments were cloned using the In-Fusion™ cloning system (Takara Bio USA, Inc) to create mutagenic libraries. The cloned inserts were transformed into chemically competent LK4 cells. The library was then screened for elevated strand displacement activity of the expressed mutant polymerases.

Assay Design: The assay design is shown in FIG. 3. Four complimentary oligonucleotides Oligo A (green), Oligo B (light blue), Oligo C (dark blue) and Locked Nucleic Acid (LNA) Oligo D (red) were annealed to each other. Oligo A is complimentary to Oligo B and initiates the polymerization reaction. Oligo B is the template and has a FAM—fluorescent reporter at the 5'-end. Oligo C is complimentary to Oligo B and has a BHQ quencher at the 3'-end. Locked Nucleic Acid Oligo D is complimentary to template Oligo B and serves as a high energy hurdle. When polymerase, $Mg^{2+}$ and nucleotides are added to the annealed mixture the polymerization reaction extends the Oligo A and the newly synthesized strand displaces the LNA Oligo D and Oligo C, thus releasing the quencher from the fluorescent probe. A fluorescent signal is generated upon completion of the cycle. The thermocycling conditions were:

Denaturation 95° C. 3"
Annealing 60° C. 5"
Extension 65° C. 30"
30 cycles

The cloned PCR fragments were sequenced to determine the mutation(s) that were present in any single clone.

Nuclease Activity. To determine nuclease activity, the extension reactions were conducted without adding dNTP's. When no dNTP's are present in the reaction, any increase in fluorescent signal is due to the nuclease activity of the enzyme. If no increase in fluorescent signal is observed, the enzyme has little to no, or substantially reduced, endonuclease and exonuclease activity.

Results: A number of clones were identified that had increased strand displacement activity compared to the parental G46E C21 polymerase. Representative plates comprising individual bacterial colonies (clones) are shown in FIGS. 4A and 4B. In summary, the following clones having increased strand displacement activity were sequenced, and have the mutations indicated (where the first number corresponds to the plate number shown in FIGS. 4A and 4B, and the letter-number (e.g., F24) corresponds to the well on the plate):

Plate 1_Clone F24: Mutations: I686V and A693V
Plate 1 Clone L3: Mutations: T516I and V633I
Plate 1_Clone P19: Mutations: Q415H, E420D, E636G, N752S, V768M
Plate 2 Clone M22: Mutations: R525G and F694S
Plate 2_Clone G9: Mutations: Q491H and T516S
Plate 2 Clone N19: Mutations: S515F and T666M
Plate 2_Clone N7: Mutations: E402V, V555A and N582D
Plate 3 Clone A24: Mutations: A737T and A759T
Plate 3_Clone F21: Mutations: L521Q and T546A
Plate 3 Clone G10: Mutations: N668S
Plate 3 Clone 114: Mutations: A456T
Plate 4_Clone G23: Mutations: K507M, T571A and S652F
Plate 4 Clone K12: Mutations: S515F and A832V
Plate 5_Clone C6: Mutations: D498E, L524V, R598G and M616I
Plate 5_Clone G20: Mutations: A444T, D498E, M660K and Y673N
Plate 5_Clone G23: Mutations: E493D, T511S, M648I and M749L
Plate 5_Clone H21: Mutations: Q635K The mutations are spread throughout the Polymerase Domain. These mutations include the following "hot spots" or stretches in the primary amino acid sequence: 515-516, 521-525, 633-636, 666-668, 693-694.

Figure 5A:
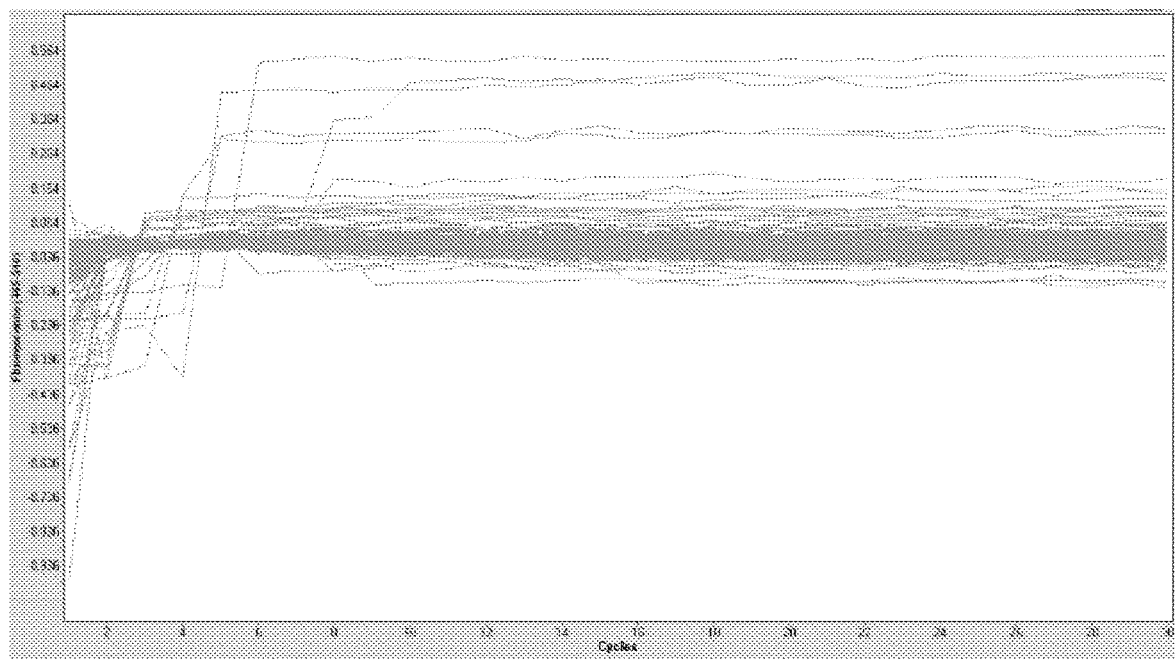
FIG. 5A and FIG. 5B provide data showing that the mutant polymerases described herein have substantially reduced endonuclease and exonuclease activity.
Figure 5B:
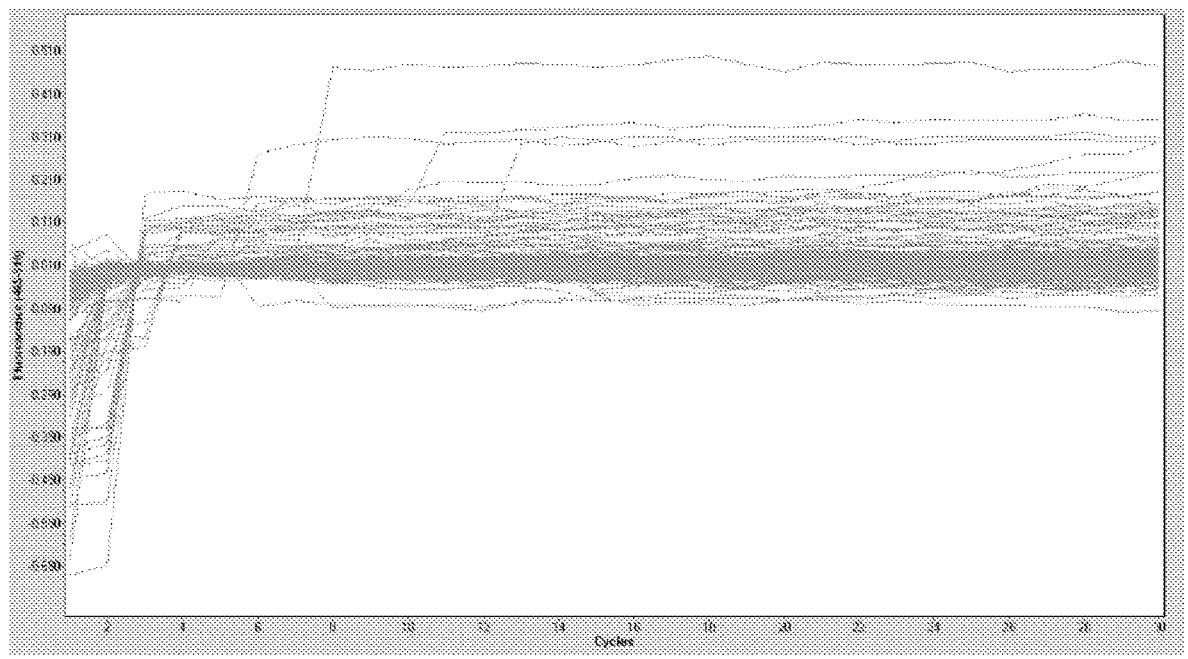

Nuclease Activity: FIGS. 5A and 5B show the result from two plates in which no dNTP's were added to the extension reactions. The majority of clones do not show any fluorescent signal. Note that some of the wells show a fluorescent signal, but it is at background level and no higher than 0.5 relative fluorescent units (RFU's).

This example demonstrates that the mutant polymerases described above have increased or enhanced strand displacement activity, as compared to the G46E parental enzyme. The mutant polymerases also function at elevated temperatures (i.e., they withstand the denaturation temperature of 95° C., annealing temperature of 60° C., and the extension temperature of 65° C. In addition, the mutant polymerases exhibit very little exonuclease or endonuclease activity.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A mutant DNA polymerase having increased 5'-3' strand displacement activity and substantially reduced 5'-3' exonuclease and endonuclease activity compared with a control DNA polymerase, wherein the amino acid sequence of the mutant DNA polymerase comprises an amino acid sequence at least 90% identical to SEQ ID NO:1 or SEQ ID NO:40, and comprises a mutation corresponding to position 498 of SEQ ID NO:1 and wherein the control DNA polymerase comprises the amino acid sequence of SEQ ID NO:40.

2. The mutant DNA polymerase of claim 1, wherein the mutation at the corresponding to position 498 of SEQ ID NO:1 from: is D498E.

3. The mutant DNA polymerase of claim 1, wherein the amino acid of the DNA polymerase corresponding to position 498 of SEQ ID NO: 1 is any amino acid other than D.

4. The mutant DNA polymerase of claim 1, wherein the amino acid sequence of the DNA polymerase comprises single and/or combinations of mutations at the corresponding positions of SEQ ID NO:1 selected from D498E, E524V, R598G and I616M.

5. The mutant DNA polymerase of claim 1, wherein the DNA polymerase comprises an amino acid sequence at least 95% identical to SEQ ID NO:40.

6. The mutant DNA polymerase of claim 1, wherein the increased 5'-3' strand displacement activity and substantially reduced 5'-3' exonuclease and endonuclease activity occur at elevated temperatures.

7. The mutant DNA polymerase of claim 1, wherein the amino acid corresponding to position 580 of SEQ ID NO:1 is any amino acid other than D.

8. The mutant DNA polymerase of claim 1, wherein the amino acid corresponding to position 580 of SEQ ID NO:1 is selected from the group consisting of L, G, T, Q, A, S, N, R, and K.

9. The mutant DNA polymerase of claim 1, wherein the amino acid corresponding to position 580 of SEQ ID NO:1 is G.

10. The mutant DNA polymerase of claim 1, wherein the amino acid corresponding to position 709 of SEQ ID NO: 1 is any amino acid other than I.

11. The mutant DNA polymerase of claim 1, wherein the amino acid corresponding to position 709 of SEQ ID NO: 1 is selected from the group consisting of K, R, S, G, and A.

12. The mutant DNA polymerase of claim 1, wherein the amino acid corresponding to position 709 of SEQ ID NO:1 is K.

13. A kit for producing an extended primer, comprising:
at least one container providing a mutant DNA polymerase as in claim 1.

14. The kit according to claim 13, further comprising one or more additional containers selected from the group consisting of:
(a) a container providing a primer hybridizable, under primer extension conditions, to a predetermined polynucleotide template;
(b) a container providing nucleoside triphosphates; and
(c) a container providing a buffer suitable for primer extension.

15. A reaction mixture comprising a mutant DNA polymerase as in claim 1, at least one primer, a polynucleotide template, and nucleoside triphosphates.

16. The reaction mixture of claim 15, further comprising a second thermostable DNA polymerase.

* * * * *

SEQUENCE LISTING

Sequence total quantity: 42
SEQ ID NO: 1          moltype = AA  length = 834
FEATURE               Location/Qualifiers
REGION                1..834

```
                    note = MISC_FEATURE - Thermus sp. Z05 DNA polymerase (Z05)
source              1..834
                    mol_type = protein
                    organism = Thermus sp.
SEQUENCE: 1
MKAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGFEAD  120
DVLATLAKKA EREGYEVRIL TADRDLYQLV SDRVAVLHPE GHLITPEWLW EKYGLKPEQW  180
VDFRALVGDP SDNLPGVKGI GEKTALKLLK EWGSLENILK NLDRVKPESV RERIKAHLED  240
LKLSLELSRV RSDLPLEVDF ARRREPDREG LRAFLERLEF GSLLHEFGLL EAPAPLEEAP  300
WPPPEGAFVG FVLSRPEPMW AELKALAACK EGRVHRAKDP LAGLKDLKEV RGLLAKDLAV  360
LALREGLDLA PSDDPMLLAY LLDPSNTTPE GVARRYGGEW TEDAAHRALL AERLQQNLLE  420
RLKGEEKLLW LYQEVEKPLS RVLAHMEATG VRLDVAYLKA LSLELAEEIR RLEEEVFRLA  480
GHPFNLNSRD QLERVLFDEL RLPALGKTQK TGKRSTSAAV LEALREAHPI VEKILQHREL  540
TKLKNTYVDP LPGLVHPRTG RLHTRFNQTA TATGRLSSSD PNLQNIPIRT PLGQRIRRAF  600
VAEAGWALVA LDYSQIELRV LAHLSGDENL IRVFQEGKDI HTQTASWMFG VSPEAVDPLM  660
RRAAKTVNFG VLYGMSAHRL SQELAIPYEE AVAFIERYFQ SFPKVRAWIE KTLEEGRKRG  720
YVETLFGRRR YVPDLNARVK SVREAAERMA FNMPVQGTAA DLMKLAMVKL FPHLREMGAR  780
MLLQVHDELL LEAPQARAEE VAALAKEAME KAYPLAVPLE VEVGIGEDWL SAKG        834

SEQ ID NO: 2        moltype = AA  length = 832
FEATURE             Location/Qualifiers
REGION              1..832
                    note = MISC_FEATURE - Thermus aquaticus DNA polymerase (Taq)
source              1..832
                    mol_type = protein
                    organism = Thermus aquaticus
SEQUENCE: 2
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KE          832

SEQ ID NO: 3        moltype = AA  length = 830
FEATURE             Location/Qualifiers
REGION              1..830
                    note = MISC_FEATURE - Thermus filiformis DNA polymerase
                    (Tfi)
source              1..830
                    mol_type = protein
                    organism = Thermus filiformis
SEQUENCE: 3
MLPLLEPKGR VLLVDGHHLA YRTFFALKGL TTSRGEPVQA VYGFAKSLLK ALKEDGEVAI   60
VVFDAKAPSF RHEAYEAYKA GRAPTPEDFP RQLALIKELV DLLGLVRLEV PGFEADDVLA  120
TLARKAEREG YEVRILSADR DLYQLLSDRI HLLHPEGWLT PGWLQERYG LSPERWVEYR  180
ALVGDPSDNL PGVPGIGEKT ALKLLKEWGS LEAILKNLDQ VKPERVWEAI RNNLDKLQMS  240
LELSRLRTDL PLEVDFAKRR EPTGKGLKAF LERLEFGSLL HEFGLLEAPK EAEEAPWPPP  300
GGAFLGFLLS RPEPMWAELL ALAGAKEGRV HRAEDPVGAL KDLKEIRGLL AKDLSVLALR  360
EGREIPPGDD PMLLAYLLDP GNTNPEGVAR RYGGEWKEDA AARALLSERL WQALYPRVAE  420
EERLLWLYRE VERPLAQVLA HMEATGVRLD VPYLEALSQE VAFELERLEA EVHRLAGHPF  480
NLNSRDQLER VLFDELGLPP IGKTEKTGKR STSAAVLELL REAHPIVGRI LEYRELMKLK  540
STYIDPLPRL VHPKTGRLHT RFNQTATATG RLSSSDPNLQ NIPVRTPLGQ RIRKAFIAEE  600
GHLLVALDYS QIELRVLAHL SGDENLIRVF REGKDIHTET AAWMFGVPPE GVDGAMRRAA  660
KTVNFGVLYG MSAHRLSQEL SIPYEEAAAF IERYFQSFPK VRAWIAKTLE EGRKKGYVET  720
LFGRRRYVPD LNARVKSVRE AAERMAFNMP VQGTAADLMK LAMVKLFPRL RPLGVRILLQ  780
VHDELVLEAP KARAEEAAQL AKETMEGVYP LSVVPLEVEVG MGEDWLSAKE            830

SEQ ID NO: 4        moltype = AA  length = 831
FEATURE             Location/Qualifiers
REGION              1..831
                    note = MISC_FEATURE - Thermus flavus DNA polymerase (Tfl)
source              1..831
                    mol_type = protein
                    organism = Thermus flavus
SEQUENCE: 4
MAMLPLFEPK GRVLLVDGHH LAYRTFFALK GLTTSRGEPV QAVYGFAKSL LKALKEDGDV   60
VVVVFDAKAP SFRHEAYEAY KAGRAPTPED FPRQLALIKE LVDLLGLVRL EVPGFEADDV  120
LATLAKRAEK EGYEVRILTA DRDLYQLLSE RIAILHPEGY LITPAWLYEK YGLRPEQWVD  180
YRALAGDPSD NIPGVKGIGE KTAQRLIREW GSLENLFQHL DQVKPSLREK LQAGMEALAL  240
```

```
SRKLSQVHTD LPLEVDFGRR RTPNLEGLRA FLERLEFGSL LHEFGLLEGP KAAEEAPWPP  300
PEGAFLGFSF SRPEPMWAEL LALAGAWEGR LHRAQDPLRG LRDLKGVRGI LAKDLAVLAL  360
REGLDLFPED DPMLLAYLLD PSNTTPEGVA RRYGGEWTED AGERALLAER LFQTLKERLK  420
GEERLLWLYE EVEKPLSRVL ARMEATGVRL DVAYLQALSL EVEAEVRQLE EEVFRLAGHP  480
FNLNSRDQLE RVLFDELGLP AIGKTEKTGK RSTSAAVLEA LREAHPIVDR ILQYRELTKL  540
KNTYIDPLPA LVHPKTGRLH TRFNQTATAT GRLSSSDPNL QNIPVRTPLG QRIRRAFVAE  600
EGWVLVVLDY SQIELRVLAH LSGDENLIRV FQEGRDIHTQ TASWMFGVSP EGVDPLMRRA  660
AKTINFGVLY GMSAHRLSGE LSIPYEEAVA FIERYFQSYP KVRAWIEGTL EEGRRRGYVE  720
TLFGRRRYVP DLNARVKSVR EAAERMAFNM PVQGTAADLM KLAMVRLFPR LQELGARMLL  780
QVHDELVLEA PKDRAERVAA LAKEVMEGVW PLQVPLEVEV GLGEDWLSAK E           831

SEQ ID NO: 5            moltype = AA  length = 830
FEATURE                 Location/Qualifiers
REGION                  1..830
                        note = MISC_FEATURE - Thermus sp. sps17 DNA polymerase
                        (Sps17)
source                  1..830
                        mol_type = protein
                        organism = Thermus sp.
SEQUENCE: 5
MLPLFEPKGR VLLVDGHHLA YRTFFALKGL TTSRGEPVQA VYGFAKSLLK ALKEDGEVAI   60
VVFDAKAPSF RHEAYEAYKA GRAPTPEDFP RQLALIKELV DLLGLVRLEV PGFEADDVLA  120
TLAKKAEREG YEVRILSADR DLYQLLSDRI HLLLHPEGEVL TPGWLQERYG LSPERWVEYR  180
ALVGDPSDNL PGVPGIGEKT ALKLLKEWGS LEAILKNLDQ VKPERVREAI RNNLDKLQMS  240
LELSRLRTDL PLEVDFAKRR EPDWEGLKAF LERLEFGSLL HEFGLLEAPK EAEEAPWPPP  300
GGAFLGPLLS RPEPMWAELL ALAGAKEGRV HRAEDPLRGL KDLKEIRGLL AKDLSVLALR  360
EGREIPPGDD PMLLAYLLDP GNTNPEGVAR RYGGEWKEDA AARALLSERL WQALYPRVAE  420
EERLLWLYRE VERPLAQVLA HMEATGVRLD VPYLEALSQE VAFELERLEA EVHRLAGHPF  480
NLNSRDQLER VLFDELGLPP IGKTEKTGKR STSAAVLELL REAHPIVGRI LEYRELMKLK  540
STYIDPLPRL VHPKTGRLHT RFNQTATATG RLSSSDPNLQ NIPVRTPLGQ RIRKAFIAEE  600
GHLLVALDYS QIELRVLAHL SGDENLIRVF REGKDIHTET AAWMFGVPPE GVDGAMRRAA  660
KTVNFGVLYG MSAHRLSQEL SIPYEEAAAF IERYFQSPPK VRAWIAKTLE EGRKKGYVET  720
LFGRRRYVPD LNARVKSVRE AAERMAFNMP VQGTAADLMK LAMVKLFPRL RPLGVRILLQ  780
VHDELVLEAP KARAEEAAQL AKETMEGVYP LSVPLEVEVG MGEDWLSAKA             830

SEQ ID NO: 6            moltype = AA  length = 834
FEATURE                 Location/Qualifiers
REGION                  1..834
                        note = MISC_FEATURE - Thermus thermophilus DNA polymerase
                        (Tth)
source                  1..834
                        mol_type = protein
                        organism = Thermus thermophilus
SEQUENCE: 6
MEAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGYEAD  120
DVLATLAKKA EKEGYEVRIL TADRDLYQLV SDRVAVLHPE GHLITPEWLW EKYGLRPEQW  180
VDFRALVGDP SDNLPGVKGI GEKTALKLLK EWGSLENLLK NLDRVKPENV REKIKAHLED  240
LRLSLELSRV RTDLPLEVDL AQGREPDREG LRAFLERLEF GSLLHEFGLL EAPAPLEEAP  300
WPPPEGAFVG FVLSRPEPMW AELKALAACR DGRVHRAADP LAGLKDLKEV RGLLAKDLAV  360
LASREGLDLV PGDDPMLLAY LLDPSNTTPE GVARRYGGEW TEDAAHRALL SERLHRNLLK  420
RLEGEEKLLW LYHEVEKPLS RVLAHMEATG VRRDVAYLQA LSLELAEEIR RLEEEVFRLA  480
GHPFNLNSRD QLERVLFDEL RLPALGKTQK TGKRSTSAAV LEALREAHPI VEKILQHREL  540
TKLKNTYVDP LPSLVHPRTG RLHTRFNQTA TATGRLSSSD PNLQNIPVRT PLGQRIRRAF  600
VAEAGWALVA LDYSQIELRV LAHLSGDENL IRVFQEGKDI HTQTASWMFG VPPEAVDPLM  660
RRAAKTVNFG VLYGMSAHRL SQELAIPYEE AVAFIERYFQ SFPKVRAWIE KTLEEGRKRG  720
YVETLFGRRR YVPDLNARVK SVREAAERMA FNMPVQGTAA DLMKLAMVKL FPRLREMGAR  780
MLLQVHDELL LEAPQARAEE VAALAKEAME KAYPLAVPLE VEVGMGEDWL SAKG         834

SEQ ID NO: 7            moltype = AA  length = 834
FEATURE                 Location/Qualifiers
REGION                  1..834
                        note = MISC_FEATURE - Thermus caldophilus DNA polymerase
                        (Tca)
source                  1..834
                        mol_type = protein
                        organism = Thermus caldophilus
SEQUENCE: 7
MEAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGYEAD  120
DVLATLAKNP EKEGYEVRIL TADRDLDQLV SDRVAVLHPE GHLITPEWLW QKYGLKPEQW  180
VDFRALVGDP SDNLPGVKGI GEKTALKLLK EWGSLENLLK NLDRVKPENV REKIKAHLED  240
LRLSLELSRV RTDLPLEVDL AQGREPDREG LRAFLERLEF GSLLHEFGLL EAPAPLEEAP  300
WPPPEGAFVG FVLSRPEPMW AELKALAACR DGRVHRAADP LAGLKDLKEV RGLLAKDLAV  360
LASREGLDLV PGDDPMLLAY LLDPSNTTPE GVARRYGGEW TEDAAHRALL SERLHRNLLK  420
RLQGEEKLLW LYHEVEKPLS RVLAHMEATG VRLDVAYLQA LSLELAEEIR RLEEEVFRLA  480
GHPFNLNSRD QLERVLFDEL RLPALGKTQK TGKRSTSAAV LEALREAHPI VEKILQHREL  540
TKLKNTYVDP LPSLVHPNTG RLHTRFNQTA TATGRLSSSD PNLQNIPVRT PLGQRIRRAF  600
VAEAGWALVA LDYSQIELRV LAHLSGDENL IRVFQEGKDI HTQTASWMFG VPPEAVDPLM  660
```

```
RRAAKTVNFG VLYGMSAHRL SQELAIPYEE AVAFIERYFQ SFPKVRAWIE KTLEEGRKRG    720
YVETLFGRRR YVPDLNARVK SVREAAERMA FNMPVQGTAA DLMKLAMVKL FPRLREMGAR    780
MLLQVHDELL LEAPQAGAEE VAALAKEAME KAYPLAVPLE VEVGMGEDWL SAKG          834

SEQ ID NO: 8              moltype = AA   length = 20
FEATURE                   Location/Qualifiers
REGION                    1..20
                          note = synthetic DNA polymerase motif
VARIANT                   1
                          note = Xaa = Leu or Ile
VARIANT                   2
                          note = Xaa = Val, Leu, Ile or Phe
VARIANT                   3
                          note = Xaa = Ala, Val, Ser or Gly
VARIANT                   4
                          note = Xaa = Leu or Ala
VARIANT                   9
                          note = Xaa = any amino acid other than Ile, Lys, Asn, Gln
                           or Thr
VARIANT                   13
                          note = Xaa = Val, Ile or Leu
VARIANT                   17
                          note = Xaa = Leu, Val or Ile
VARIANT                   18
                          note = Xaa = Ser or Ala
VARIANT                   19
                          note = Xaa = Gly, Lys, Asp or Glu
source                    1..20
                          mol_type = protein
                          organism = synthetic construct
SEQUENCE: 8
XXXXDYSQXE LRXLAHXXXD                                                20

SEQ ID NO: 9              moltype = AA   length = 20
FEATURE                   Location/Qualifiers
REGION                    1..20
                          note = synthetic DNA polymerase motif
VARIANT                   3
                          note = Xaa = Ala or Val
VARIANT                   9
                          note = Xaa = any amino acid other than Ile, Lys, Asn, Gln
                           or Thr
source                    1..20
                          mol_type = protein
                          organism = synthetic construct
SEQUENCE: 9
LVXLDYSQXE LRVLAHLSGD                                                20

SEQ ID NO: 10             moltype = AA   length = 20
FEATURE                   Location/Qualifiers
REGION                    1..20
                          note = synthetic DNA polymerase motif
VARIANT                   9
                          note = Xaa = any amino acid other than Ile, Lys, Asn, Gln
                           or Thr
source                    1..20
                          mol_type = protein
                          organism = synthetic construct
SEQUENCE: 10
LVALDYSQXE LRVLAHLSGD                                                20

SEQ ID NO: 11             moltype = AA   length = 20
FEATURE                   Location/Qualifiers
REGION                    1..20
                          note = synthetic DNA polymerase motif
source                    1..20
                          mol_type = protein
                          organism = synthetic construct
SEQUENCE: 11
LVALDYSQME LRVLAHLSGD                                                20

SEQ ID NO: 12             moltype = AA   length = 38
FEATURE                   Location/Qualifiers
REGION                    1..38
                          note = synthetic polymerase domain region of Thermus sp.
                           Z05 DNA polymerase (Z05)
source                    1..38
                          mol_type = protein
                          organism = synthetic construct
```

```
SEQUENCE: 12
RRAFVAEAGW ALVALDYSQI ELRVLAHLSG DENLIRVF                              38

SEQ ID NO: 13           moltype = AA  length = 38
FEATURE                 Location/Qualifiers
REGION                  1..38
                        note = synthetic polymerase domain region of Thermus
                        aquaticus DNA polymerase (Taq)
source                  1..38
                        mol_type = protein
                        organism = synthetic construct
SEQUENCE: 13
RRAFIAEEGW LLVALDYSQI ELRVLAHLSG DENLIRVF                              38

SEQ ID NO: 14           moltype = AA  length = 38
FEATURE                 Location/Qualifiers
REGION                  1..38
                        note = synthetic polymerase domain region of Thermus
                        filiformus DNA polymerase (Tfi)
source                  1..38
                        mol_type = protein
                        organism = synthetic construct
SEQUENCE: 14
RKAFIAEEGH LLVALDYSQI ELRVLAHLSG DENLIRVF                              38

SEQ ID NO: 15           moltype = AA  length = 38
FEATURE                 Location/Qualifiers
REGION                  1..38
                        note = synthetic polymerase domain region of Thermus flavus
                        DNA polymerase (Tfl)
source                  1..38
                        mol_type = protein
                        organism = synthetic construct
SEQUENCE: 15
RRAFVAEEGW VLVVLDYSQI ELRVLAHLSG DENLIRVF                              38

SEQ ID NO: 16           moltype = AA  length = 38
FEATURE                 Location/Qualifiers
REGION                  1..38
                        note = synthetic polymerase domain region of Thermus sp.
                        sps17 DNA polymerase (Sps17)
source                  1..38
                        mol_type = protein
                        organism = synthetic construct
SEQUENCE: 16
RKAFIAEEGH LLVALDYSQI ELRVLAHLSG DENLIRVF                              38

SEQ ID NO: 17           moltype = AA  length = 38
FEATURE                 Location/Qualifiers
REGION                  1..38
                        note = synthetic polymerase domain region of Thermus
                        thermophilus DNA polymerase (Tth)
source                  1..38
                        mol_type = protein
                        organism = synthetic construct
SEQUENCE: 17
RRAFVAEAGW ALVALDYSQI ELRVLAHLSG DENLIRVF                              38

SEQ ID NO: 18           moltype = AA  length = 38
FEATURE                 Location/Qualifiers
REGION                  1..38
                        note = synthetic polymerase domain region of Thermus
                        caldophilus DNA polymerase (Tca)
source                  1..38
                        mol_type = protein
                        organism = synthetic construct
SEQUENCE: 18
RRAFVAEAGW ALVALDYSQI ELRVLAHLSG DENLIRVF                              38

SEQ ID NO: 19           moltype = AA  length = 39
FEATURE                 Location/Qualifiers
REGION                  1..39
                        note = synthetic polymerase domain region of Thermotoga
                        maritima DNA polymerase (Tma)
source                  1..39
                        mol_type = protein
                        organism = synthetic construct
SEQUENCE: 19
RKAIVPQDPN WWIVSADYSQ IELRILAHLS GDENLLRAF                             39
```

```
SEQ ID NO: 20          moltype = AA   length = 39
FEATURE                Location/Qualifiers
REGION                 1..39
                       note = synthetic polymerase domain region of Thermotoga
                        neopolitana DNA polymerase (Tne)
source                 1..39
                       mol_type = protein
                       organism = synthetic construct
SEQUENCE: 20
RKAIVPQDPD WWIVSADYSQ IELRILAHLS GDENLVKAF                              39

SEQ ID NO: 21          moltype = AA   length = 39
FEATURE                Location/Qualifiers
REGION                 1..39
                       note = synthetic polymerase domain region of Thermosipho
                        africanus DNA polymerase (Taf)
source                 1..39
                       mol_type = protein
                       organism = synthetic construct
SEQUENCE: 21
RKAVRPQRQD WWILGADYSQ IELRVLAHVS KDENLLKAF                              39

SEQ ID NO: 22          moltype = AA   length = 8
FEATURE                Location/Qualifiers
REGION                 1..8
                       note = synthetic conserved DNA polymerase active site motif
                        A
source                 1..8
                       mol_type = protein
                       organism = synthetic construct
SEQUENCE: 22
DYSQIELR                                                                8

SEQ ID NO: 23          moltype = AA   length = 38
FEATURE                Location/Qualifiers
REGION                 1..38
                       note = synthetic polymerase domain region of Deinococcus
                        radiodurans DNA polymerase (Dra)
source                 1..38
                       mol_type = protein
                       organism = synthetic construct
SEQUENCE: 23
RKGFIAEDGF TLIAADYSQI ELRLLAHIAD DPLMQQAF                               38

SEQ ID NO: 24          moltype = AA   length = 39
FEATURE                Location/Qualifiers
REGION                 1..39
                       note = synthetic polymerase domain region of Bacillus
                        stearothermophilus DNA polymerase (Bst)
source                 1..39
                       mol_type = protein
                       organism = synthetic construct
SEQUENCE: 24
RQAFVPSEPD WLIFAADYSQ IELRVLAHIA EDDNLIEAF                              39

SEQ ID NO: 25          moltype = AA   length = 39
FEATURE                Location/Qualifiers
REGION                 1..39
                       note = synthetic polymerase domain region of Bacillus
                        caldotenax DNA polymerase (Bca)
source                 1..39
                       mol_type = protein
                       organism = synthetic construct
SEQUENCE: 25
RQAFVPSESD WLIFAADYSQ IELRVLAHIA EDDNLMEAF                              39

SEQ ID NO: 26          moltype = AA   length = 20
FEATURE                Location/Qualifiers
REGION                 1..20
                       note = synthetic polymerase domain region native consensus
                        motif
VARIANT                1
                       note = Xaa = Leu or Ile
VARIANT                2
                       note = Xaa = Val, Leu, Ile or Phe
VARIANT                3
                       note = Xaa = Ala, Val, Ser or Gly
VARIANT                4
```

|  |  |
|---|---|
| VARIANT | 13 |
|  | note = Xaa = Leu or Ala |
| VARIANT | 17 |
|  | note = Xaa = Val, Ile or Leu |
| VARIANT | 18 |
|  | note = Xaa = Leu, Val or Ile |
| VARIANT | 19 |
|  | note = Xaa = Ser or Ala |
|  | note = Xaa = Gly, Lys, Asp or Glu |
| source | 1..20 |
|  | mol_type = protein |
|  | organism = synthetic construct |

SEQUENCE: 26
XXXXDYSQIE LRXLAHXXXD                                               20

| SEQ ID NO: 27 | moltype = AA  length = 893 |
|---|---|
| FEATURE | Location/Qualifiers |
| REGION | 1..893 |
|  | note = synthetic chimeric CS5 DNA polymerase derived from N-terminal 5'-nuclease domain of Thermus sp. Z05 and C-terminal 3'-5' exonuclease and polymerase domains of Thermotoga maritima DNA polymerases |
| source | 1..893 |
|  | mol_type = protein |
|  | organism = synthetic construct |

SEQUENCE: 27
MKAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGFEAD  120
DVLATLAKKA EREGYEVRIL TADRDLYQLV SDRVAVLHPE GHLITPEWLW EKYGLKPEQW  180
VDFRALVGDP SDNLPGVKGI GEKTALKLLK EWGSLENILK NLDRVKPESV RERIKAHLED  240
LKLSLELSRV RSDLPLEVDF ARRREPDREG LRAFLERLEF GSLLHEFGLL EESEPVGYRI  300
VKDLVEFEKL IEKLRESPSF AIDLETSSLD PFDCDIVGIS VSFKPKEAYY IPLHHRNAQN  360
LDEKEVLKKL KEILEDPGAK IVGQNLKFDY KVLMVKGVEP VPPYFDTMIA AYLLEPNEKK  420
FNLDDLALKF LGYKMTSYQE LMSFSFPLFG FSFADVPVEK AANYSCEDAD ITYRLYKTLS  480
LKLHEADLEN VFYKIEMPLV NVLARMELNG VYVVDTEFLKK LSEEYGKKLE ELAEEIYRIA  540
GEPFNINSPK QVSRILFEKL GIKPRGKTTK TGDYSTRIEV LEELAGEHEI IPLILEYRKI  600
QKLKSTYIDA LPKMVNPKTG RIHASFNQTG TATGRLSSSD PNLQNLPTKS EEGKEIRKAI  660
VPQDPNWWIV SADYSQIELR ILAHLSGDEN LLRAFEEGID VHTLTASRIF NVKPEEVTEE  720
MRRAGKMVNF SIIYGVTPYG LSVRLGVPVK EAEKMIVNYF VLYPKVRDYI QRVVSEAKEK  780
GYVRTLFGRK RDIPQLMARD RNTQAEGERI AINTPIQGTA ADIIKLAMIE IDRELKERKM  840
RSKMIIQVHD ELVFEVPNEE KDALVELVKD RMTNVVKLSV PLEVDVTIGK TWS         893

| SEQ ID NO: 28 | moltype = AA  length = 893 |
|---|---|
| FEATURE | Location/Qualifiers |
| REGION | 1..893 |
|  | note = synthetic chimeric CS6 DNA polymerase derived from N-terminal 5'-nuclease domain of Thermus sp. Z05 and C-terminal 3'-5' exonuclease and polymerase domains of Thermotoga maritima DNA polymerases |
| source | 1..893 |
|  | mol_type = protein |
|  | organism = synthetic construct |

SEQUENCE: 28
MKAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGFEAD  120
DVLATLAKKA EREGYEVRIL TADRDLYQLV SDRVAVLHPE GHLITPEWLW EKYGLKPEQW  180
VDFRALVGDP SDNLPGVKGI GEKTALKLLK EWGSLENILK NLDRVKPESV RERIKAHLED  240
LKLSLELSRV RSDLPLEVDF ARRREPDREG LRAFLERLEF GSLLHEFGLL EESEPVGYRI  300
VKDLVEFEKL IEKLRESPSF AIALATSSLD PFDCDIVGIS VSFKPKEAYY IPLHHRNAQN  360
LDEKEVLKKL KEILEDPGAK IVGQNLKFDY KVLMVKGVEP VPPYFDTMIA AYLLEPNEKK  420
FNLDDLALKF LGYKMTSYQE LMSFSFPLFG FSFADVPVEK AANYSCEDAD ITYRLYKTLS  480
LKLHEADLEN VFYKIEMPLV NVLARMELNG VYVVDTEFLKK LSEEYGKKLE ELAEEIYRIA  540
GEPFNINSPK QVSRILFEKL GIKPRGKTTK TGDYSTRIEV LEELAGEHEI IPLILEYRKI  600
QKLKSTYIDA LPKMVNPKTG RIHASFNQTG TATGRLSSSD PNLQNLPTKS EEGKEIRKAI  660
VPQDPNWWIV SADYSQIELR ILAHLSGDEN LLRAFEEGID VHTLTASRIF NVKPEEVTEE  720
MRRAGKMVNF SIIYGVTPYG LSVRLGVPVK EAEKMIVNYF VLYPKVRDYI QRVVSEAKEK  780
GYVRTLFGRK RDIPQLMARD RNTQAEGERI AINTPIQGTA ADIIKLAMIE IDRELKERKM  840
RSKMIIQVHD ELVFEVPNEE KDALVELVKD RMTNVVKLSV PLEVDVTIGK TWS         893

| SEQ ID NO: 29 | moltype = AA  length = 19 |
|---|---|
| FEATURE | Location/Qualifiers |
| REGION | 1..19 |
|  | note = synthetic DNA polymerase motif |
| VARIANT | 1 |
|  | note = Xaa = Ala, Asp, Ser, Glu, Arg or Gln |
| VARIANT | 2 |
|  | note = Xaa = Trp or Tyr |
| VARIANT | 3 |
|  | note = Xaa = any amino acid other than Ile, Leu or Met |

-continued

```
VARIANT                      4
                             note = Xaa = Glu, Ala, Gln, Lys, Asn or Asp
VARIANT                      5
                             note = Xaa = Lys, Gly, Arg, Gln, His or Asn
VARIANT                      6
                             note = Xaa = Thr, Val, Met or Ile
VARIANT                      7
                             note = Xaa = Leu, Val or Lys
VARIANT                      8
                             note = Xaa = Glu, Ser, Ala, Asp or Gln
VARIANT                      9
                             note = Xaa = Glu or Phe
VARIANT                      10
                             note = Xaa = Gly or Ala
VARIANT                      11
                             note = Xaa = Arg or Lys
VARIANT                      12
                             note = Xaa = Lys, Arg, Glu, Thr or Gln
VARIANT                      13
                             note = Xaa = Arg, Lys or His
VARIANT                      17
                             note = Xaa = Glu, Arg or Thr
source                       1..19
                             mol_type = protein
                             organism = synthetic construct
SEQUENCE: 29
XXXXXXXXX XXXGYVXTL                                                          19

SEQ ID NO: 30                moltype = DNA   length = 21
FEATURE                      Location/Qualifiers
misc_feature                 1..21
                             note = synthetic error-prone (mutagenic) PCR amplification
                                forward primer
source                       1..21
                             mol_type = other DNA
                             organism = synthetic construct
SEQUENCE: 30
ctacctcctg gaccnctcca a                                                      21

SEQ ID NO: 31                moltype = DNA   length = 25
FEATURE                      Location/Qualifiers
misc_feature                 1..25
                             note = synthetic error-prone (mutagenic) PCR amplification
                                reverse primer
source                       1..25
                             mol_type = other DNA
                             organism = synthetic construct
SEQUENCE: 31
ataaccaact ggtagtggcg tgtaa                                                  25

SEQ ID NO: 32                moltype = AA   length = 921
FEATURE                      Location/Qualifiers
REGION                       1..921
                             note = MISC_FEATURE - Deinococcus radiodurans DNA
                                polymerase (Dra)
source                       1..921
                             mol_type = protein
                             organism = Deinococcus radiodurans
SEQUENCE: 32
MADASPDPSK PDALVLIDGH ALAFRSYFAL PPLNNSKGEM TDAIVGFMKL LLRLARQKSN    60
QVIVVFDPPV KTLRHEQYEG YKSGRAQTPE DLRGQINRIR ALVDALGPPR LEEPGYEADD   120
VIASLTRMAE GKGYEVRIVT SDRDAYQLLD EHVKVIANDF SLIGPAQVEE KYGVTVRQWV   180
DYRALTGDAS DNIPGAKGIG PKTAAKLLQE YGTLEKVYEA AHAGTLKPDG TRKKLLDSEE   240
NVKFSHDLSC MVTDLPLDIE FGVRRLPDNP LVTEDLLTEL ELHSLRPMIL GLNGPEQDGH   300
APDDLLEREH AQTPEEDEAA ALPAFSAPEL AEWQTPAEGA VWGYVLSRED DLTAALLAAA   360
TFEDGVARPA RVSEPDEWAQ AEAPENLFGE LLPSDKPLTK KEQKALEKAQ KDAEKARAKL   420
REQFPATVDE AEFVGQRTVT AAAAKALAAH LSVRGTVVEP GDDPLLYAYL LDPANTNMPV   480
VAKRYLDREW PADAPTRAAI TGHLVRELPP LLDDARRKMY DEMEKPLSGV LGRMEVRGVQ   540
VDSDFLQTLS IQAGVRLADL ESQIHEYAGE EPHIRSPKQL ETVLYDKLEL ASSKKTKLTG   600
QRSTAVSALE PLRDAHPIIP LVLEFRELDK LRGTYLDPIP NLVNPHTGRL HTTFAQTAVA   660
TGRLSSLNPN LQNIPIRSEL GREIRKGFIA EDGFTLIAAD YSQIELRLLA HIADDPLMQQ   720
AFVEGADIHR RTAAQVLGLD EATVDANQRR AAKTVNFGVL YGMSAHRLSN DLGIPYAEAA   780
TFIEIYFATY PGIRRYINHT LDFGRTHGYV ETLYGRRRYV PGLSSRNRVQ REAEERLAYN   840
MPIQGTAADI MKLAMVQLDP QLDAIGARML LQVHDELLIE APLDKAEQVA ALTKKVMENV   900
VQLKVPLAVE VGTGPNWFDT K                                              921

SEQ ID NO: 33                moltype = AA   length = 892
FEATURE                      Location/Qualifiers
REGION                       1..892
```

```
                          note = MISC_FEATURE - Thermosipho africanus DNA polymerase
                              (Taf)
source                    1..892
                          mol_type = protein
                          organism = Thermosipho africanus
SEQUENCE: 33
MGKMFLFDGT GLVYRAFYAI DQSLQTSSGL HTNAVYGLTK MLIKFLKEHI SIGKDACVFV    60
LDSKGGSKKR KDILETYKAN RPSTPDLLLE QIPYVEELVD ALGIKVLKIE GFEADDIIAT   120
LSKKFESDFE KVNIITGDKD LLQLVSDKVF VWRVERGITD LVLYDRNKVI EKYGIYPEQF   180
KDYLSLVGDQ IDNIPGVKGI GKKTAVSLLK KYNSLENVLK NINLLTEKLR RLLEDSKEDL   240
QKSIELVELI YDVPMDVEKD EIIYRGYNPD KLLKVLKKYE FSSIIKELNL QEKLEKEYIL   300
VDNEDKLKKL AEEIEKYKTF SIDTETTSLD PFEAKLVGIS ISTMEGKAYY IPVSHFGAKN   360
ISKSLIDKFL KQILQEKDYN IVGQNLKFDY EIFKSMGFSP NVPHFDTMIA AYLLNPDEKR   420
FNLEELSLKY LGYKMISFDE LVNENVPLFG NDFSYVPLER AVEYSCEDAD VTYRIFRKLG   480
RKIYENEMEK LFYEIEMPLI DVLSEMELNG VYFDEEYLKE LSKKYQEKMD GIKEKVFEIA   540
GETFNLNSST QVAYILFEKL NIAPYKKTAT GKFSTNAEVL EELSKEHEIA KLLLEYRKYQ   600
KLKSTYIDSI PLSINRKTNR VHTTFHQTGT STGRLSSSNP NLQNLPTRSE EGKEIRKAVR   660
PQRQDWWILG ADYSQIELRV LAHVSKDENL LKAFKEDLDI HTIITAAKIFG VSEMFVSEQM   720
RRVGKMVNFA IIYGVSPYGL SKRIGLSVSE TKKIIDNYFR YYKGVFEYLK RMKDEARKKG   780
YVTTLFGRRR YIPQLRSKNG NRVQEGERIA VNTPIQGTAA DIIKIAMINI HNRLKKENLR   840
SKMILQVHDE LVFEVPDNEL EIVKDLVRDE MENAVKLDVP LKVDVYYGKE WE           892

SEQ ID NO: 34             moltype = AA   length = 893
FEATURE                   Location/Qualifiers
REGION                    1..893
                          note = MISC_FEATURE - Thermotoga maritima DNA polymerase
                              (Tma)
source                    1..893
                          mol_type = protein
                          organism = Thermotoga maritima
SEQUENCE: 34
MARLFLFDGT ALAYRAYYAL DRSLSTSTGI PTNATYGVAR MLVRFIKDHI IVGKDYVAVA    60
FDKKAATFRH KLLETYKAQR PKTPDLLIQQ LPYIKKLVEA LGMKVLEVEG YEADDIIATL   120
AVKGLPLFDE IFIVTGDKDM LQLVNEKIKV WRIVKGISDL ELYDAQKVKE KYGVEPQQIP   180
DLLLALTGDEI DNIPGVTGIG EKTAVQLLEK YKDLEDILNH VRELPQKVRK ALLRDRENAI   240
LSKKLAILET NVPIEINWEE LRYQGYDREK LLPLLKELEF ASIMKELQLY EESEPVGYRI   300
VKDLVEFEKL IEKLRESPSF AIDLETSSLD PFDCDIVGIS VSFKPKEAYY IPLHHRNAQN   360
LDEKEVLKKL KEILEDPGAK IVGQNLKFDY KVLMVKGVEV VPPYFDTMIA AYLLEPNEKK   420
FNLDDLALKF LGYKMTSYQE LMSFSFPLFG FSFADVPVEK AANYSCEDAD ITYRLYKTLS   480
LKLHEADLEN VFYKIEMPLV NVLARMELNG VYVDTEFLKK LSEEYGKKLE ELAEEIYRIA   540
GEPFNINSPK QVSRILFEKL GIKPRGKTTK TGDYSTRIEV LEELAGEHEI IPLILEYRKI   600
QKLKSTYIDA LPKMVNPKTG RIHASFNQTG TATGRLSSSD PNLQNLPTKS EEGKEIRKAI   660
VPQDPNWWIV SADYSQIELR ILAHLSGDEN LLRAFEEGID VHTLTASRIF NVKPEEVTEE   720
MRRAGKMVNF SIIYGVTPYG LSVRLGDVPVK EAEKMIVNYF VLYPKVRDYI QRVVSEAKEK   780
GYVRTLFGRK RDIPQLMARD RNTQAEGERI AINTPIQGTA ADIIKLAMIE IDRELKERKM   840
RSKMIIQVHD ELVFEVPNEE KDALVELVKD RMTNVVKLSV PLEVDVTIGK TWS           893

SEQ ID NO: 35             moltype = AA   length = 893
FEATURE                   Location/Qualifiers
REGION                    1..893
                          note = MISC_FEATURE - Thermotoga neopolitana DNA polymerase
                              (Tne)
source                    1..893
                          mol_type = protein
                          organism = Thermotoga neopolitana
SEQUENCE: 35
MARLFLFDGT ALAYRAYYAL DRSLSTSTGI PTNAVYGVAR MLVKFIKEHI IPEKDYAAVA    60
FDKKAATFRH KLLVSDKAQR PKTPALLVQQ LPYIKRLIEA LGFKVLELEG YEADDIIATL   120
AVRAARFLMR FSLITGDKDM LQLVNEKIKV WRIVKGISDL ELYDSKKVKE RYGVEPHQIP   180
DLLLALTGDDI DNIPGVTGIG EKTAVQLLGK YRNLEYILEH ARELPQRVRK ALLRDREVAI   240
LSKKLATLVT NAPVEVDWEE MKYRGYDKRK LLPILKELEF ASIMKELQLY EEAEPTGYEI   300
VKDHKTFEDL IEKLKEVPSF ALDLETSSLD PFNCEIVGIS VSFKPKTAYY IPLHHRNAHN   360
LDETLVLSKL KEILEDPSSK IVGQNLKYDY KVLMVKGISP VPHFDTMIA AYLLEPNEKK    420
FNLEDLSLKF LGYKMTSYQE LMSFSSPLFG FSFADVPVDK AAEYSCEDAD ITYRLYKILS   480
MKLHEAALEN VFYRIEMPLV NVLARMEFNW VYVDTEFLKK LSEEYGKKLE ELAEKIYQIA   540
GEPFNINSPK QVSNILFEKL GIKPRGKTTK TGDYSTRIEV LEEIANEHEI VPLILEFRKI   600
LKLKSTYIDT LPKLVNPKTG RFHASFHQTG TATGRLSSSD PNLQNLPTKS EEGKEIRKAI   660
VPQDPDWWIV SADYSQIELR ILAHLSGDEN LVKAFEEGID VHTLTASRIF NVKPEEVNEE   720
MRRVGKMVNF SIIYGVTPYG LSVRLGIPVK EAEKMIISYF TLYPKVRSYI QQVVAEAKEK   780
GYVRTLFGRK RDIPQLMARD KNTQSEGERI AINTPIQGTA ADIIKLAMID IDEELRKRNM   840
KSRMIIQVHD ELVFEVPDEE KEELVDLVKN KMTNVVKLSV PLEVDISIGK SWS           893

SEQ ID NO: 36             moltype = AA   length = 876
FEATURE                   Location/Qualifiers
REGION                    1..876
                          note = MISC_FEATURE - Bacillus stearothermophilus DNA
                              polymerase (Bst)
source                    1..876
                          mol_type = protein
```

```
                          organism = Bacillus stearothermophilus
SEQUENCE: 36
MKNKLVLIDG NSVAYRAFFA LPLLHNDKGI HTNAVYGFTM MLNKILAEEQ PTHILVAFDA    60
GKTTFRHETF QDYKGGRQQT PPELSEQFPL LRELLKAYRI PAYELDHYEA DDIIGTMAAR   120
AEREGFEVKV ISGDRDLTQL ASPQVTVEIT KKGITDIESY TPETVVEKYG LTPEQIVDLK   180
GLMGDKSDNI PGVPGIGEKT AVKLLKQFGT VENVLASIDE IKGEKLKENL RQYRDLALLS   240
KQLAAICRDA PVELTLDDIV YKGEDREKVV ALFQELGFQS FLDKMAVQTD EGEKPLAGMD   300
FAIADSVTDE MLADKAALVV EVVGDNYHHA PIVGIALANE RGRFFLRPET ALADPKFLAW   360
LGDETKKKTM FDSKRAAVAL KWKGIELRGV VFDLLLAAYL LDPAQAAGDV AAVAKMHQYE   420
AVRSDEAVYG KGAKRTVPDE PTLAEHLARK AAAIWALEEP LMDELRRNEQ DRLLTELEQP   480
LAGILANMEF TGVKVDTKRL EQMGAELTEQ LQAVERRIYE LAGQEFNINS PKQLGTVLFD   540
KLQLPVLKKT KTGYSTSADV LEKLAPHHEI VEHILHYRQL GKLQSTYIEG LLKVVHPVTG   600
KVHTMFNQAL TQTGRLSSVE PNLQNIPIRL EEGRKIRQAF VPSEPDWLIF AADYSQIELR   660
VLAHIAEDDN LIEAFRRGLD IHTKTAMDIF HVSEEDVTAN MRRQAKAVNF GIVYGISDYG   720
LAQNLNITRK EAAEFIERYF ASFPGVKQYM DNIVQEAKQK GYVTTLLHRR RYLPDITSRN   780
FNVRSFAERT AMNTPIQGSA ADIIKKAMID LSVRLREERL QARLLLQVHD ELILEAPKEE   840
IERLCRLVPE VMEQAVALRV PLKVDYHYGP TWYDAK                             876

SEQ ID NO: 37           moltype = AA  length = 877
FEATURE                 Location/Qualifiers
REGION                  1..877
                        note = MISC_FEATURE - Bacillus caldotenax DNA polymerase
                          (Bca)
source                  1..877
                        mol_type = protein
                        organism = Bacillus caldotenax
SEQUENCE: 37
MKKKLVLIDG SSVAYRAFFA LPLLHNDKGI HTNAVYGFTM MLNKILAEEE PTHMLVAFDA    60
GKTTFRHEAF QEYKGGRQQT PPELSEQFPL LRELLRAYRI PAYELENYEA DDIIGTLAAR   120
AEQEGFEVKV ISGDRDLTQL ASPHVTVDIT KKGITDIEPY TPEAVREKYG LTPEQIVDLK   180
GLMGDKSDNI PGVPGIGEKT AVKLLRQFGT VENVLASIDE IKGEKLKETL RQHREMALLS   240
KKLAAIRRDA PVELSLDDIA YQGEDREKVV ALFKELGFQS FLEKMESPSS EEEKPLAKMA   300
FTLADRVTEE MLADKAALVV EVVEENYHDA PIVGIAVVNE HGRFFLRPET ALADPQFVAW   360
LGDETKKKSM FDSKRAAVAL KWKGIELCGV SFDLLLAAYL LDPAQGVDDV AAAAKMQYE    420
AVRPDEAVYG KGAKRAVPDE PVLAEHLVRK AAAIWALERP FLDELRRNEQ DRLLVELEQP   480
LSSILAEMEF AGVKVDTKRL EQMGEELAEQ LRTVEQRIYE LAGQEFNINS PKQLGVILFE   540
KLQLPVLKKS KTGYSTSADV LEKLAPYHEI VENILQHYRQ LGKLQSTYIE GLLKVVRPDT   600
KKVHTIFNQA LTQTGRLSST EPNLQNIPIR LEEGRKIRQA FVPSESDWLI FAADYSQIEL   660
RVLAHIAEDD NLMEAFRRDL DIHTKTAMDI FQVSEDEVTP NMRRQAKAVN FGIVYGISDY   720
GLAQNLNISR KEAAEFIERY FESFPGVKRY MENIVQEAKQ KGYVTTLLHR RRYLPDITSR   780
NFNVRSFAER MAMNTPIQGS AADIIKKAMI DLNARLKEER LQARLLLQVH DELILEAPKE   840
EMERLCRLVP EVMEQAVTLR VPLKVDYHYG STWYDAK                            877

SEQ ID NO: 38           moltype = AA  length = 13
FEATURE                 Location/Qualifiers
REGION                  1..13
                        note = synthetic polymerase motif corresponding to the
                          D580X mutation of Z05
VARIANT                 7
                        note = Xaa = Ser or Thr
VARIANT                 8
                        note = Xaa = any amino acid other than Asp or Glu
source                  1..13
                        mol_type = protein
                        organism = synthetic construct
SEQUENCE: 38
TGRLSSXXPN LQN                                                      13

SEQ ID NO: 39           moltype = AA  length = 831
FEATURE                 Location/Qualifiers
REGION                  1..831
                        note = MISC_FEATURE - Carboxydothermus hydrogenoformans DNA
                          polymerase (Chy)
source                  1..831
                        mol_type = protein
                        organism = Carboxydothermus hydrogenoformans
SEQUENCE: 39
MGKVVLVDGN SLLHRAFFAL PPLKTTKGEP TGAVYEFLTM LFRVIKDEKP EYLAVAFDIS    60
RKTFRTEQFT AYKGHRKEAP DELVPQFALV REVLKVLNVP YIELDGYEAD DIIGHLSRAF   120
AGQGHEVVIY TADRDMLQLV DEKTVVYLTK KGITELVKMD LAAILENYGL KPKQLVDVKG   180
LMGDPSDNIP GVPGIGEKTA LDLIKTYGSV EEVLARKDEL KPKLREKLAE HENLAKISKQ   240
LATILREIPL EISLEDLKVK EPNYEEVAKL FLHLEFKSFL KEIEPKIKKE YQEGKDLVQV   300
ETVETEGQIA VVFSDGFYVD DGEKTKFYSL DRLNEIEEIF RNKKIITDDA KGIYHVCLEK   360
GLTFPEVCFD ARIAAYVLNP ADQNPGLKGL YLKYDLPVYE DVSLNIRGLF YLKKEMMRKI   420
FEQEQERLFY EIELPLTPVL AQMEHTGIQV DREALKEMSL ELGEQIEELI REIYVLAGEE   480
FNLNSPRQLG VILFEKLGLP VIKKTKTGYS TDAEVLEELL PFHEIIGKIL NYRQLMKLKS   540
TYTDGLMPLI NERTGKLHTT FNQTGTLTGR LASSEPNLQN IPIRLELGRK LRKMFIPSPG   600
YDYIVSADYS QIELRLLAHF SEEPKLIEAY QKGEDIHRKT ASEVFGVSLE EVTPEMRAHA   660
KSVNFGIVYG ISDFGLGRDL KIPREVAGKY IKNYFANYPK VREYLDELVR TAREKGYVTT   720
```

```
LFGRRRYIPE LSSKNRTVQG FGERTAMNTP LQGSAADIIK LAMINVEKEL KARKLKSRLL   780
LSVHDELVLE VPAEELEEVK ALVKGVMESV VELKVPLIAE VGAGKNWYEA K            831

SEQ ID NO: 40              moltype = AA  length = 834
FEATURE                    Location/Qualifiers
REGION                     1..834
                           note = Synthetic G42E C21 DNA Polymerase
source                     1..834
                           mol_type = protein
                           organism = synthetic construct
SEQUENCE: 40
MKAMLPLFEP KGRVLLVDGH HLAYRTFFAL KGLTTSRGEP VQAVYEFAKS LLKALKEDGY    60
KAVFVVFDAK APSFRHEAYE AYKAGRAPTP EDFPRQLALI KELVDLLGFT RLEVPGFEAD   120
DVLATLAKKA EREGYEVRIL TADRDLYQLV SDRVAVLHPE GHLITPEWLW EKYGLKPEQW   180
VDFRALVGDP SDNLPGVKGI GEKTALKLLK EWGSLENILK NLDRVKPESV RERIKAHLED   240
LKLSLELSRV RSDLPLEVDF ARRREPDREG LRAFLERLEF GSLLHEFGLL EAPAPLEEAP   300
WPPPEGAFVG FVLSRPEPMW AELKALAACK EGRVHRAKDP LAGLKDLKEV RGLLAKDLAV   360
LALREGLDLA PSDDPMLLAY LLDPSNTTPE GVARRYGGEW TEDAAHRALL AERLQQNLLE   420
RLKGEEKLLW LYQEVEKPLS RVLAHMEATG VRLDVAYLKA LSLELAEEIR RLEEEVFRLA   480
GHPFNLNSRD QLERVLFDEL RLPALGKTQK TGKRSTSAAV LEALREAHPI VEKILQHREL   540
TKLKNTYVDP LPGLVHPRTG RLHTRFNQTA TATGRLSSSD PNLQNIPIRT PLGQRIRRAF   600
VAEAGWALVA LDYSQIELRV LAHLSGDENL IRVFQEGKDI HTQTASWMFG VSPEAVDPLM   660
RRAAKTVNFG VLYGMSAHRL SQELAIPYEE AVAFIERYFQ SFPKVRAWIE KTLEEGRKRG   720
YVETLFGRRR YVPDLNARVK SVREAAERMA FNMPVQGTAA DLMKLAMVKL FPHLREMGAR   780
MLLQVHDELL LEAPQARAEE VAALAKEAME KAYPLAVPLE VEVGIGEDWL SAKG         834

SEQ ID NO: 41              moltype = DNA  length = 2505
FEATURE                    Location/Qualifiers
misc_feature               1..2505
                           note = Synthetic Nucleic acid sequence encoding C21
                            polymerase
source                     1..2505
                           mol_type = other DNA
                           organism = synthetic construct
SEQUENCE: 41
atgaaagcta tgttaccatt attcgaaccc aaaggccggg tcctcctggt ggacggccac     60
cacctggcct accgcacctt cttcgccctg aagggcctca ccacgagccg gggcgaaccg    120
gtgcaggcgg tttacggctt cgccaagagc tcctcaagg  ccctgaagga ggacgggtac    180
aaggccgtct tcgtggtctt tgacgccaag gccccttcct tccgccacga ggcctacgaa    240
gcctacaagg caggccgcgc cccgaccccc gaggacttcc ccggcagct  cgccctcatc    300
aaggagctgg tggacctcct ggggtttact cgcctcgagg ttccgggctt tgaggcggac    360
gacgtcctcc ccaccctggc caagaaggcg gaaagggagg gtacgaggt  cgcatcctc    420
accgccgacc gggaccctta ccagtctcgtc ccgaccgcg tcgccgtcct ccaccccggg    480
ggccacctca tcaccccgga gtggctttgg gagaagtacg gccttaagcc ggagcagtgg    540
gtggacttcc gcgcccttgt gggggacccc tccgacaacc tccccgggg  caagggcatc    600
ggggagaaga ccgccctcaa gctcctcaag gagtggggaa gcctggaaaa tatcctcaag    660
aacctggacc gggtgaagcc ggaaagcgtc cggaaaagga tcaaggccca cctggaaagc    720
cttaagctct ccttggagct ttccggggtg cgctcggacc tccccctgga ggtgacttc     780
gcccggagc  gggagcctga ccgggaaggg cttcgggcct ttttggagcg cttggagttc    840
ggcagcctcc tccacgagtt cggcctcctc gaggcccccg cccccctgga ggaggccccc    900
tggccccgc  cggaagggc  cttcgtgggc ttcgtcctct cccgcccga  gccatgtgg     960
gcggagctta agccctggcc cgcctgcaag gagggccggg tgcaccggc  aaaggacccc   1020
ttggcggggc taaaggacct caaggagtc  cgaggcctcc tcgccaagga cctgccgtt    1080
ttggcccttc gcgagggggct ggacctcgcg ccttcggacg accccatgct cctcgcctac   1140
ctcctggacc cctccaacac cacccccgag ggggtggcc  ggctacgg  ggggagtgg    1200
acggaggacg ccgccaccg  ggccctcctc gctgagggc  tccagcaaaa cctcttggaa   1260
cgcctcaagg gagaggaaaa gctcctttgg ctctaccaag aggtggaaaa gcccctctcc   1320
cgggtcctgg cccacatgga ggccaccggg gtaaggctgg acgtggccta tctaaaggcc   1380
ctttccctgg agcttgcgga ggagattcgc cgcctcgagg aggaggtctt ccgcctggcg   1440
ggccacccct tcaacctgaa ctcccgtgac cagctagagc gggtgctctt tgacgagctt   1500
aggcttcccg ccctgggcaa gacgcaaaag acggggaagc gctccaccag cgccgcggtg   1560
ctggaggccc tcagggaggc cacccccatc gtggagaaga tcctccagca ccgggagctc   1620
accaagctca gaacaccta  cgtagacccc ctccgggccc tcgtcacccc gaggacgggc   1680
cgcctccaca cccgcttcaa ccagacagcc acggccacgg gaaggctctc tagctccgga   1740
cccaacctgc agaacatccc catccgcacc cccttgggcc agaggatccg ccggcccttc   1800
gtggccgagg cggatgggc  gttggtggcc ctggactata gccagatgga gctccgggtc   1860
ctcgcccacc tctccgggga cgagaacctg atcagggtct tccaggaggg gaaggacatc   1920
cacacccaga ccgcaagctg gatgttcggc gtctcccgg  aggccgtgga cccccctgatg   1980
cgccggggca ccaagacggt gaacttcggc gtcctctacg gcatgtccgc ccataggctc   2040
tcccaggagc ttgccatccc ctacgaggag gcggtggcct ttatagagcg ctacttccaa   2100
agcttccccca aggtgcgcgc ctggaaagaa aagaccctgg aggaggggag gaagcggggc   2160
tacgtggaaa ccctcttcgg aagaaggcgc tacgtgcccg acctcaacgc ccgggtgaag   2220
agcgtcaggg aggccgcgga gcgcatggcc ttcaacatgc ccgtccaggg caccgccgcc   2280
gacctcatga agctggccat ggtgaagctt ttccccccac ggctggagat gggggccggg   2340
atgctcctcc aggtcacga  cgagctcctc ctgaggcccc ccaagcgcg  ggccgaggag   2400
gtgcggctt  tggccaagga ggccatggag aaggcctacc cctcgccgt  gcccctggag   2460
gtggaggtgg ggatcgggga ggactggctt tccgccaagg gctga                   2505

SEQ ID NO: 42              moltype = AA  length = 834
```

```
FEATURE             Location/Qualifiers
REGION              1..834
                    note = Synthetic C21 polymerase with I709K mutation
source              1..834
                    mol_type = protein
                    organism = synthetic construct
SEQUENCE: 42
MKAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGFEAD  120
DVLATLAKKA EREGYEVRIL TADRDLYQLV SDRVAVLHPE GHLITPEWLW EKYGLKPEQW  180
VDFRALVGDP SDNLPGVKGI GEKTALKLLK EWGSLENILK NLDRVKPESV RERIKAHLED  240
LKLSLELSRV RSDLPLEVDF ARRREPDREG LRAFLERLEF GSLLHEFGLL EAPAPLEEAP  300
WPPPEGAFVG FVLSRPEPMW AELKALAACK EGRVHRAKDP LAGLKDLKEV RGLLAKDLAV  360
LALREGLDLA PSDDPMLLAY LLDPSNTTPE GVARRYGGEW TEDAAHRALL AERLQQNLLE  420
RLKGEEKLLW LYQEVEKPLS RVLAHMEATG VRLDVAYLKA LSLELAEEIR RLEEEVFRLA  480
GHPFNLNSRD QLERVLFDEL RLPALGKTQK TGKRSTSAAV LEALREAHPI VEKILQHREL  540
TKLKNTYVDP LPGLVHPRTG RLHTRFNQTA TATGRLSSSG PNLQNIPIRT PLGQRIRRAF  600
VAEAGWALVA LDYSQMELRV LAHLSGDENL IRVFQEGKDI HTQTASWMFG VSPEAVDPLM  660
RRAAKTVNFG VLYGMSAHRL SQELAIPYEE AVAFIERYFQ SFPKVRAWKE KTLEEGRKRG  720
YVETLFGRRR YVPDLNARVK SVREAAERMA FNMPVQGTAA DLMKLAMVKL FPHLREMGAR  780
MLLQVHDELL LEAPQARAEE VAALAKEAME KAYPLAVPLE VEVGIGEDWL SAKG        834
```